United States Patent
Mastrototaro et al.

(10) Patent No.: US 7,946,985 B2
(45) Date of Patent: May 24, 2011

(54) METHOD AND SYSTEM FOR PROVIDING SENSOR REDUNDANCY

(75) Inventors: John J. Mastrototaro, Los Angeles, CA (US); Richard K. Yoon, Northridge, CA (US); Desmond Barry Keenan, Sherman Oaks, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 713 days.

(21) Appl. No.: 11/618,260

(22) Filed: Dec. 29, 2006

(65) Prior Publication Data
US 2008/0161664 A1 Jul. 3, 2008

(51) Int. Cl.
*A61B 5/00* (2006.01)
(52) U.S. Cl. .......... 600/365; 600/319; 600/347
(58) Field of Classification Search .......... 600/347, 600/365; 714/819
See application file for complete search history.

(56) References Cited

U.S. PATENT DOCUMENTS

| | | | |
|---|---|---|---|
| 3,621,357 A | 11/1971 | Kubo et al. |
| 3,826,887 A | 7/1974 | Pemberton |
| 3,834,617 A | 9/1974 | Dyntar |
| 3,986,571 A | 10/1976 | Strobel et al. |
| 4,055,175 A | 10/1977 | Clemens et al. |
| 4,080,966 A | 3/1978 | McNally et al. |
| 4,245,634 A | 1/1981 | Albisser et al. |
| 4,280,494 A | 7/1981 | Cosgrove, Jr. et al. |
| 4,291,692 A | 9/1981 | Bowman et al. |
| 4,786,394 A | 11/1988 | Enzer et al. |
| 5,050,612 A | 9/1991 | Matsumura |
| 5,068,536 A | 11/1991 | Rosenthal |
| 5,497,772 A | 3/1996 | Schulman et al. |
| 5,507,288 A | 4/1996 | Böcker et al. |
| 5,569,186 A | 10/1996 | Lord et al. |
| 5,586,553 A | 12/1996 | Halili et al. |
| 5,665,065 A | 9/1997 | Colman et al. |
| 5,680,409 A * | 10/1997 | Qin et al. .......... 714/799 |
| 5,695,464 A | 12/1997 | Viallet |
| 5,745,362 A | 4/1998 | Hiroi et al. |
| 5,771,890 A | 6/1998 | Tamada |
| 5,813,403 A | 9/1998 | Soller et al. |
| 5,822,715 A | 10/1998 | Worthington et al. |
| 5,830,133 A | 11/1998 | Osten et al. |
| 5,885,211 A | 3/1999 | Eppstein et al. |
| 5,956,501 A | 9/1999 | Brown |

(Continued)

FOREIGN PATENT DOCUMENTS

| | | |
|---|---|---|
| DE | 10006044 A1 | 8/2001 |
| EP | 1077636 B1 | 1/2004 |
| WO | 9958050 A1 | 11/1999 |
| WO | 0074753 A1 | 12/2000 |
| WO | 03080157 A1 | 10/2003 |
| WO | 2004060455 A1 | 7/2004 |
| WO | 2006099151 A2 | 9/2006 |
| WO | 2008088490 A1 | 7/2008 |

OTHER PUBLICATIONS

Von Woedtke, et al., "In situ calibration of implanted electrochemical glucose sensors," Biomed. Biochim. Acta, 48 (11-12), 943-952 (1989).

(Continued)

*Primary Examiner* — John P Lacyk
*Assistant Examiner* — Carrie Dorna

(57) ABSTRACT

A closed loop system or semi-closed loop system for infusing insulin using sensor values applies a redundant sensor system as a fail-safe method against sensor failure. The redundant glucose sensors are used corroborate each other and a failing sensor is detected if the sensors no longer corroborate each other. The use of redundant sensors has the additional benefit of producing better sensor signals compared to the use of a single sensor.

21 Claims, 18 Drawing Sheets

U.S. PATENT DOCUMENTS

| | | | |
|---|---|---|---|
| 6,001,065 | A | 12/1999 | DeVito |
| 6,049,727 | A | 4/2000 | Crothall |
| 6,088,608 | A | 7/2000 | Schulman et al. |
| 6,180,416 | B1 | 1/2001 | Kurnik et al. |
| 6,233,471 | B1 | 5/2001 | Berner et al. |
| 6,233,539 | B1 | 5/2001 | Brown |
| 6,272,364 | B1 | 8/2001 | Kurnik |
| 6,326,160 | B1 | 12/2001 | Dunn et al. |
| 6,379,301 | B1 | 4/2002 | Worthington et al. |
| 6,416,293 | B1 | 7/2002 | Bouchard et al. |
| 6,424,873 | B1 | 7/2002 | Przybylski |
| 6,544,212 | B2 | 4/2003 | Galley et al. |
| 6,558,351 | B1 | 5/2003 | Steil et al. |
| 6,595,919 | B2 | 7/2003 | Berner et al. |
| 7,167,818 | B2 | 1/2007 | Brown |
| 7,267,665 | B2 | 9/2007 | Steil et al. |
| 7,295,867 | B2 | 11/2007 | Berner et al. |
| 7,354,420 | B2 | 4/2008 | Steil et al. |
| 7,402,153 | B2 | 7/2008 | Steil et al. |
| 2001/0016682 | A1 | 8/2001 | Berner et al. |
| 2003/0130616 | A1 | 7/2003 | Steil et al. |
| 2003/0153820 | A1 | 8/2003 | Berner et al. |
| 2003/0153821 | A1 | 8/2003 | Berner et al. |
| 2004/0193025 | A1 | 9/2004 | Steil et al. |
| 2005/0027180 | A1 | 2/2005 | Goode, Jr. et al. |
| 2005/0272640 | A1 | 12/2005 | Doyle, III et al. |
| 2006/0224109 | A1 | 10/2006 | Steil et al. |
| 2007/0038053 | A1 | 2/2007 | Berner et al. |
| 2007/0173761 | A1 | 7/2007 | Kanderian, Jr. et al. |
| 2008/0188796 | A1 | 8/2008 | Steil et al. |

OTHER PUBLICATIONS

Poitout, V., et al., "Calibration in dogs of a subcutaneous miniaturized glucose sensor using a glucose meter for blood glucose determination," Biosensors & Bioelectronics 7:587-592 (1992).

Velho, G., et al., "Strategies for calibrating a subcutaneous glucose sensor," Biomed. Biochim. Acta 48(11-12):957-964 (1989).

Schmidtke, D.W., et al., "Accuracy of the One-Point in Vivo Calibration of "Wired" Glucose Oxidase Electrodes Implanted in Jugular Veins of Rats in Periods of Rapid Rise and Decline of the Glucose Concentration," Anal. Chem. 70:2149-2155 (1998).

Csöregi, E., et al., "Design, Characterization, and One-Point in Vivo Calibration of a Subcutaneously Implanted Glucose Electrode," Anal. Chem. 66:3131-3138 (1994).

Bellazzi, R., et al., "The Subcutaneous Route to Insulin-Dependent Diabetes Therapy", IEEE Engineering in Medicine and Biology, pp. 54-64 (Jan./Feb. 2001).

Parker, R.S., et al., "The Intravenous Route to Blood Glucose Control", IEEE Engineering in Medicine and Biology, pp. 65-73 (Jan./Feb. 2001).

Olthuis, W., et al., "pH Sensor Properties of Electrochemically Grown Iridium Oxide", Sensors and Actuators B, 2 (1990), pp. 247-256.

Olthuis, W., et al., "Preparation of Iridium Oxide and its Application in Sensor-Actuator Systems," Sensors and Actuators B, 4 (1991), pp. 151-156.

Once Daily Glucotrol XL® (glipiside) extended release, May 1996; 45(suppl 2): 123A, Abstract 450.

PCT International Search Report for International Application No. PCT/US03/41650.

PCT International Search Report for International Application No. PCT/US00/15393.

PCT International Search Report and Written Opinion for International Application No. PCT/US2007/024915.

EP Examination Report and Written Opinion for Application No. 03815006.6.

PCT International Search Report and Written Opinion for International Application No. PCT/US2008/055437.

U.S. Appl. No. 60/085,344, filed May 13, 1998.

* cited by examiner

METHOD AND SYSTEM FOR PROVIDING SENSOR REDUNDANCY

FIELD

This invention relates to sensor systems in closed loop or semi-closed loop applications and more specifically to systems for predicting sensor values and detecting the failure of a sensor.

BACKGROUND

Over the years, body characteristics have been determined by obtaining a sample of bodily fluid. For example, diabetics often test for blood glucose levels. Traditional blood glucose determinations have utilized a finger prick using a lancet to withdraw a small blood sample. These systems are designed to provide data at discrete points and do not provide continuous data to show the variations in the characteristic between testing times. These discrete measurements are good to give some idea on how one's blood glucose values are at a point in time, and thus, enough information for a diabetic to give "correction" amounts of insulin to reduce their current blood glucose reading. However, these discrete readings are not able to provide enough information for any type of automatic or semi-automatic system of giving insulin based on blood glucose values.

Recently, a variety of implantable electrochemical sensors have been developed for detecting and/or quantifying specific agents or compositions in a patient's blood or interstitial fluid. For instance, glucose sensors are being developed for use in obtaining an indication of blood glucose levels in a diabetic patient. These glucose sensors connected (wired or wirelessly) to a blood glucose monitor can provide continuous glucose readings over a period of time such as 3 to 5 days. Such readings are useful in monitoring and/or adjusting a treatment regimen which typically includes the regular administration of insulin to the patient. Thus, blood glucose readings improve medical therapies with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994, which are herein incorporated by reference. Typical thin film sensors are described in commonly assigned U.S. Pat. Nos. 5,390,671; 5,391,250; 5,482,473; and 5,586,553 which are incorporated by reference herein. See also U.S. Pat. No. 5,299,571. In addition, characteristic glucose monitors used to provide continuous glucose data are described in commonly assigned U.S. patent application Ser. No. 11/322,568 entitled "Telemetered Characteristic Monitor System and Method of Using the Same" filed on Dec. 30, 2005, which is herein incorporated by reference in its entirety. In addition, infusion pumps receiving sensor data is described in commonly assigned U.S. patent application Ser. No. 10/867,529 entitled "System for Providing Blood Glucose Measurements to an Infusion Device" filed on Oct. 14, 2004, which is herein incorporated by reference in its entirety.

As sensor technology improves, there is greater desire to use the sensor values to control the infusion of drugs and medicine, like insulin in a closed loop or semi-closed loop system. Specifically, a closed loop system for diabetes would entail a glucose sensor and an insulin infusion pump attached to a patient, where the delivery of insulin would be automatically administered by the controller of the infusion pump based on the sensor's glucose value readings. A semi-closed system would typically include a patient intervention step where the amount of insulin to be infused as calculated by the controller of the infusion pump would require a patient acceptance before delivery. However, given the ramifications of over-delivery and/or under delivery of medication, no one has yet to develop a viable way to actually create a working closed loop/semi-closed loop system where obtained sensor values can be trusted enough to be used to control the delivery of medication such as insulin with sufficient safeguards to operate on its own or even with a patient confirm/decline step.

SUMMARY

According to an embodiment of the invention, a closed loop infusion system and method for controlling blood glucose concentration in the body of a user is described. Embodiments of the present invention include obtaining a first glucose reading from a first glucose sensor located at a first site and obtaining a second glucose reading from a second glucose sensor located at a second site. In preferred embodiments, the system and method corroborate the signals generated by the first and second sensors. In an embodiment, the corroboration is performed by deriving a first predictive value to the first glucose reading using the second glucose reading as an input and deriving a second predictive value to the second glucose reading using the first glucose reading as an input. A first error between the first predictive value and the first glucose reading and a second error between the second predictive value and the second glucose reading are determined. By comparing a sum of the absolute error values of the first and second errors to a threshold, a failing sensor can be identified.

According to another embodiment of the invention, the system and method determine whether the first glucose sensor or second glucose sensor has the least error in the sensor signal and calculates a reported blood glucose value based on the glucose sensor having the least error in the sensor signal. In further embodiments, a comparison to a meter glucose value can be used to determine if the first or second glucose sensor is failing.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several Figures.

FIG. 3 (b) is a side cross-sectional view of the glucose sensor system of FIG. 3 (a).

FIG. 3 (c) is a perspective view of a sensor set of the glucose sensor system of FIG. 3 (a) for use in an embodiment of the present invention.

FIG. 3 (d) is a side cross-sectional view of the sensor set of FIG. 3 (c).

DETAILED DESCRIPTION

Figure 1:
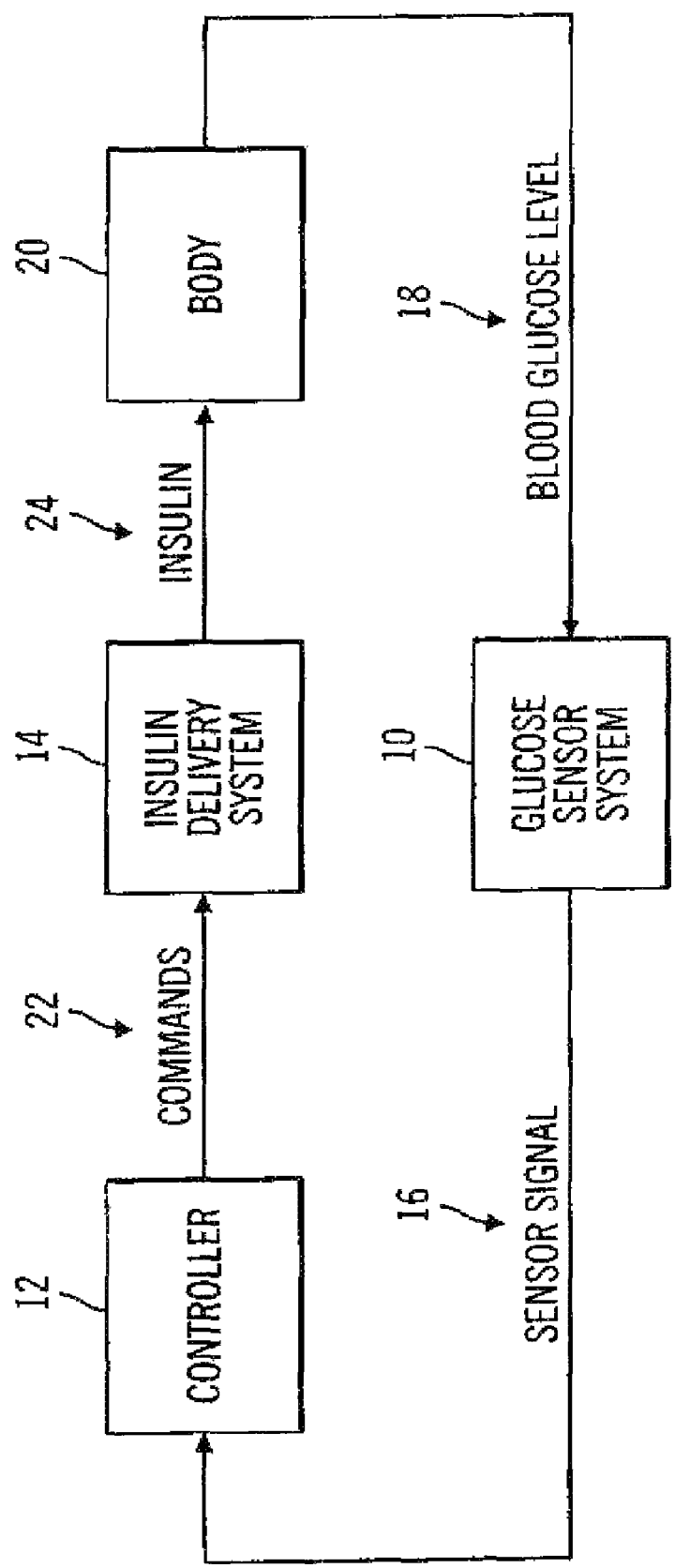
FIG. 1 is a block diagram of a closed loop glucose control system in accordance with an embodiment of the present invention.

As shown in the drawings for purposes of illustration, the invention is embodied in a closed loop infusion system for regulating the rate of fluid infusion into a body of a user based on feedback from an analyte concentration measurement taken from the body. In particular embodiments, the invention is embodied in a control system for regulating the rate of insulin infusion into the body of a user based on a glucose concentration measurement taken from the body. In preferred embodiments, the system is designed to model a pancreatic beta cell (β-cell). In other words, the system controls an infusion device to release insulin into a body of a user in a similar concentration profile as would be created by fully functioning human β-cells when responding to changes in blood glucose concentrations in the body.

Thus, the system simulates the body's natural insulin response to blood glucose levels and not only makes efficient use of insulin, but also accounts for other bodily functions as well since insulin has both metabolic and mitogenic effects. However, the algorithms must model the β-cells closely, since algorithms that are designed to minimize glucose excursions in the body, without regard for how much insulin is delivered, may cause excessive weight gain, hypertension, and atherosclerosis. In preferred embodiments of the present invention, the system is intended to emulate the in vivo insulin secretion pattern and to adjust this pattern consistent with the in vivo β-cell adaptation experienced by normal healthy individuals. The in vivo β-cell response in subjects with normal glucose tolerance (NGT), with widely varying insulin sensitivity ($S_I$), is the optimal insulin response for the maintenance of glucose homeostasis.

Preferred embodiments include a glucose sensor system 10, a controller 12 and an insulin delivery system 14, as shown in FIG. 1. The glucose sensor system 10 generates a sensor signal 16 representative of blood glucose levels 18 in the body 20, and provides the sensor signal 16 to the controller 12. The controller 12 receives the sensor signal 16 and generates commands 22 that are communicated to the insulin delivery system 14. The insulin delivery system 14 receives the commands 22 and infuses insulin 24 into the body 20 in response to the commands 22. In an alternative semi-closed loop embodiment, the commands 22 would have to be confirmed by the user before the insulin delivery system 14 would infuse insulin.

Generally, the glucose sensor system 10 includes a glucose sensor, sensor electrical components to provide power to the sensor and generate the sensor signal 16, a sensor communication system to carry the sensor signal 16 to the controller 12, and a sensor system housing for the electrical components and the sensor communication system.

Typically, the controller 12 includes controller electrical components and software to generate commands for the insulin delivery system 14 based on the sensor signal 16, and a controller communication system to receive the sensor signal 16 and carry commands to the insulin delivery system 14.

Generally, the insulin delivery system 14 includes an infusion device and an infusion tube to infuse insulin 24 into the body 20. In particular embodiments, the infusion device includes infusion electrical components to activate an infusion motor according to the commands 22, an infusion communication system to receive the commands 22 from the controller 12, and an infusion device housing to hold the infusion device.

In preferred embodiments, the controller 12 is housed in the infusion device housing and the infusion communication system is an electrical trace or a wire that carries the commands 22 from the controller 12 to the infusion device. In alternative embodiments, the controller 12 is housed in the sensor system housing and the sensor communication system is an electrical trace or a wire that carries the sensor signal 16 from the sensor electrical components to the controller electrical components. In other alternative embodiments, the controller 12 has its own housing or is included in a supplemental device. In another alternative embodiment, the controller is located with the infusion device and the sensor system all within one housing. In further alternative embodiments, the sensor, controller, and/or infusion communication systems may utilize a cable, a wire, fiber optic lines, RF, IR, or ultrasonic transmitters and receivers, or the like instead of the electrical traces.

System Overview

Figure 2:
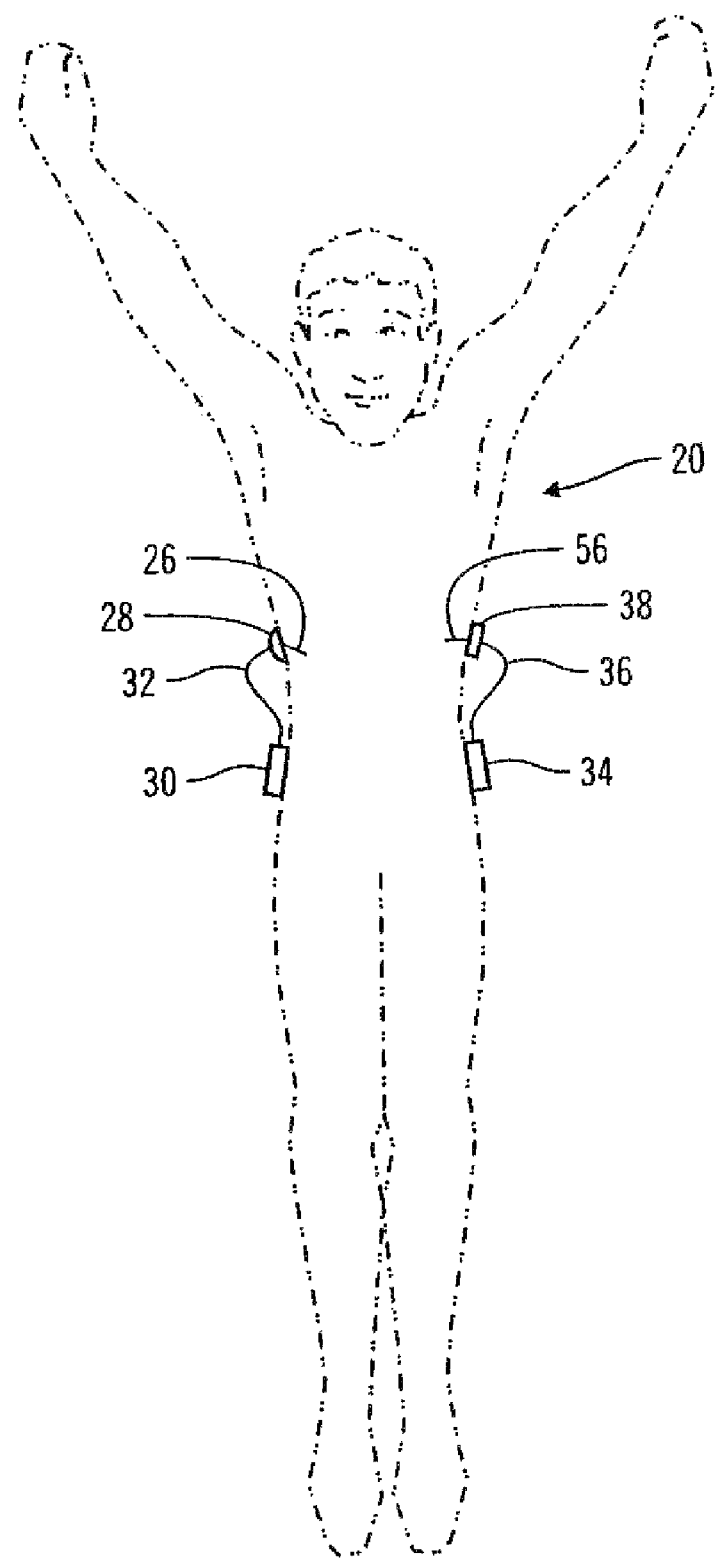
FIG. 2 is a front view of closed loop hardware located on a body in accordance with an embodiment of the present invention.
Figure 3:
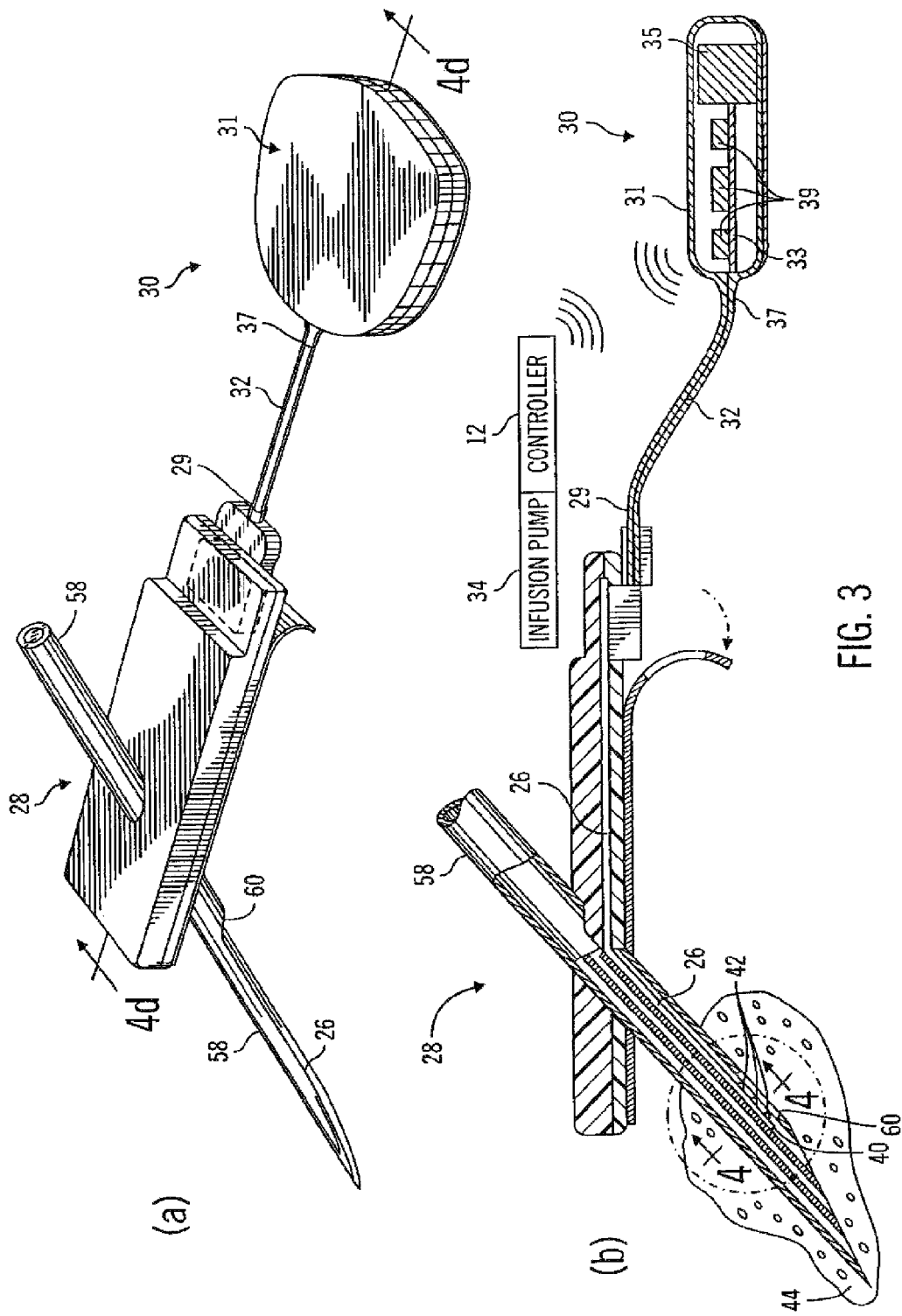
FIG. 3 (a) is a perspective view of a glucose sensor system for use in an embodiment of the present invention.
Figure 3:
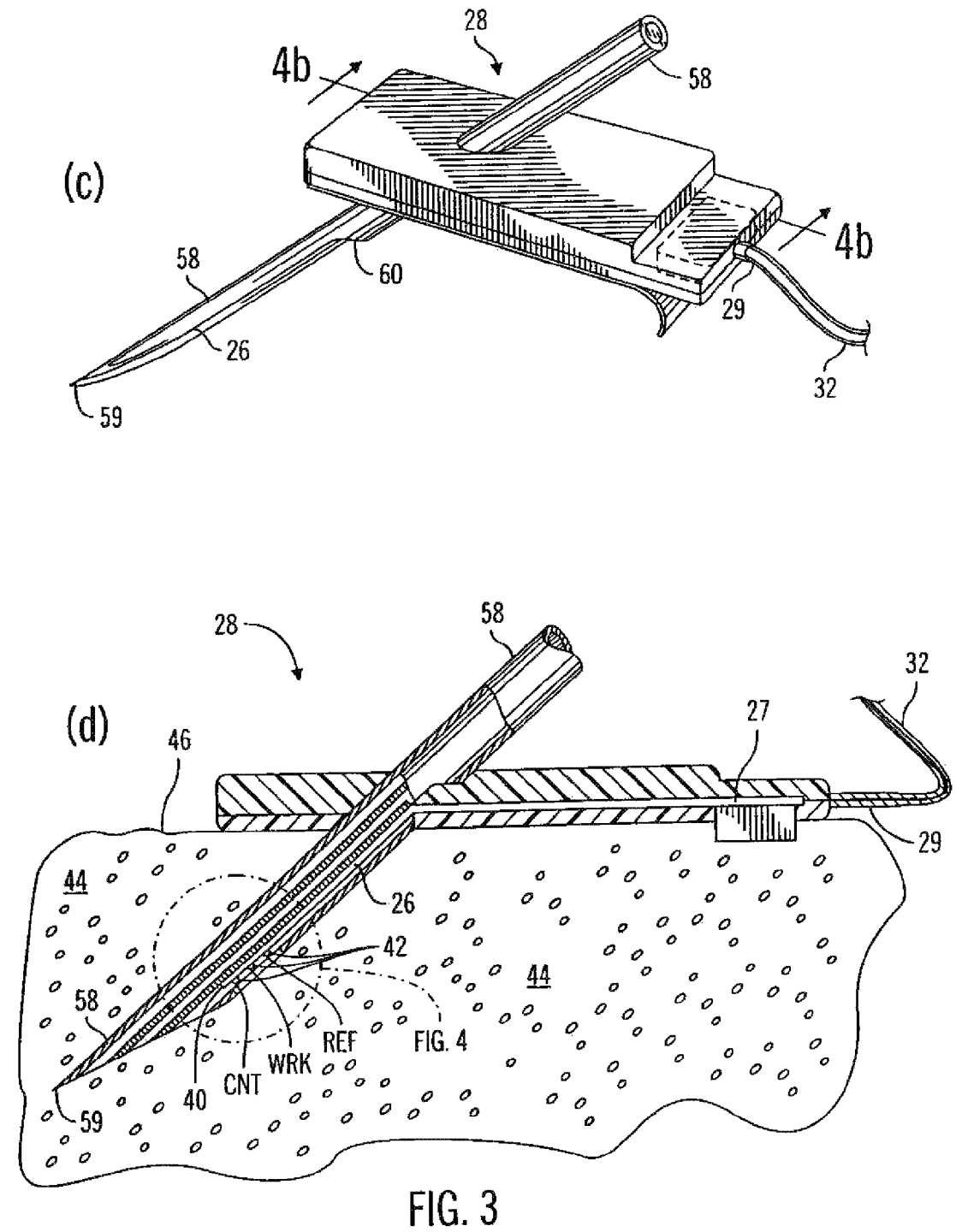
Figure 4:
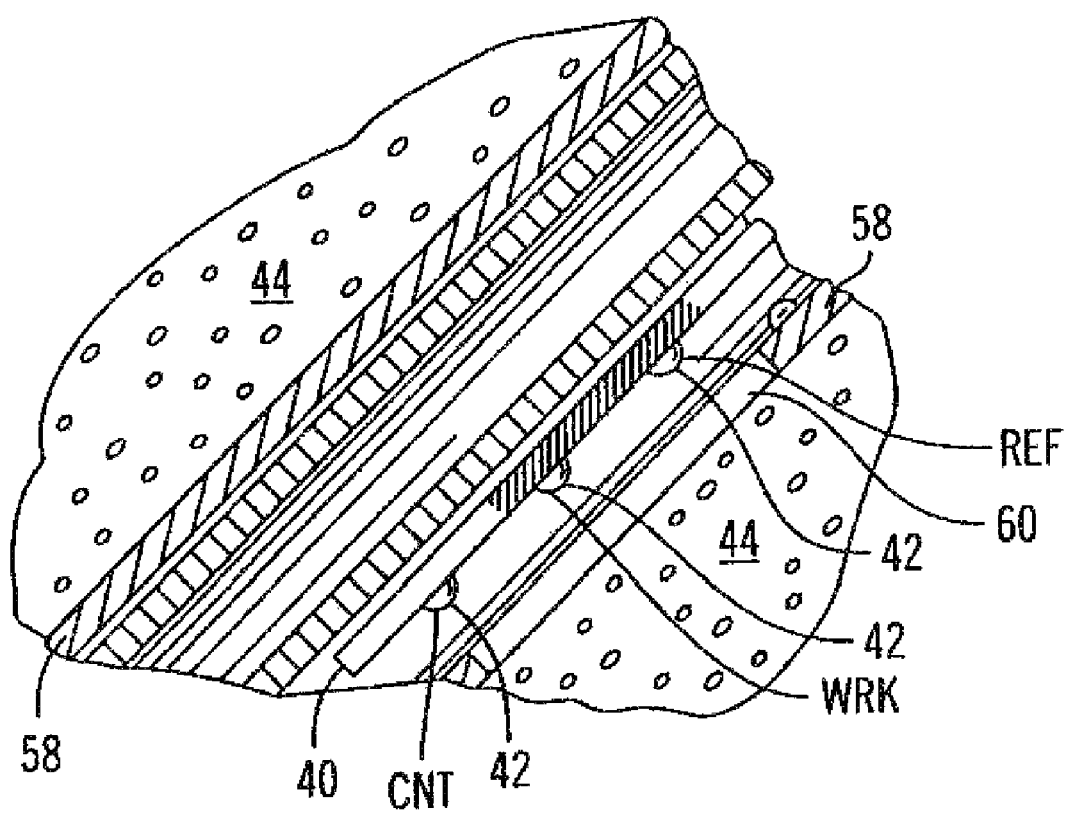
FIG. 4 is a cross sectional view of a sensing end of the sensor of FIG. 3 (d).

Preferred embodiments of the invention include a sensor 26, a sensor set 28, a telemetered characteristic monitor transmitter 30, a sensor cable 32, an infusion device 34, an infusion tube 36, and an infusion set 38, all worn on the body 20 of a user, as shown in FIG. 2. The telemetered characteristic monitor transmitter 30 includes a transmitter housing 31 that supports a printed circuit board 33, batteries 35, antenna (not shown), and a sensor cable connector (not shown), as seen in FIGS. 3 (a) and 3 (b). The sensor set 28 includes an insertion needle 58 and a cannula. A sensing end 40 of the sensor 26 has exposed electrodes 42 and is inserted through skin 46 into a subcutaneous tissue 44 of a user's body 20, as shown in FIGS. 3 (d) and 4. The needle 58 has a sharpened tip 59 that is used to facilitate placement of the cannula at the subcutaneous insertion site. After insertion, the insertion needle 58 is withdrawn to leave the cannula with the sensing end 40 and the sensor electrodes 42 in place at the selected insertion site. The electrodes 42 are in contact with interstitial fluid (ISF) that is present throughout the subcutaneous tissue 44 through a window 60 formed in the cannula. The sensor 26 is held in place by the sensor set 28, which is adhesively secured to the user's skin 46, as shown in FIGS. 3 (c) and 3 (d). The sensor set 28 provides for a connector end 27 of the sensor 26 to connect to a first end 29 of the sensor cable 32. A second end 37 of the sensor cable 32 connects to the transmitter housing 31. The batteries 35 included in the transmitter housing 31 provide power for the sensor 26 and electrical components 39 on the printed circuit board 33. The electrical components 39 sample the sensor signal 16 and store digital sensor values (Dsig) in a memory and then periodically transmit the digital sensor values Dsig from the memory to the controller 12, which is included in the infusion device 34.

Figure 5:
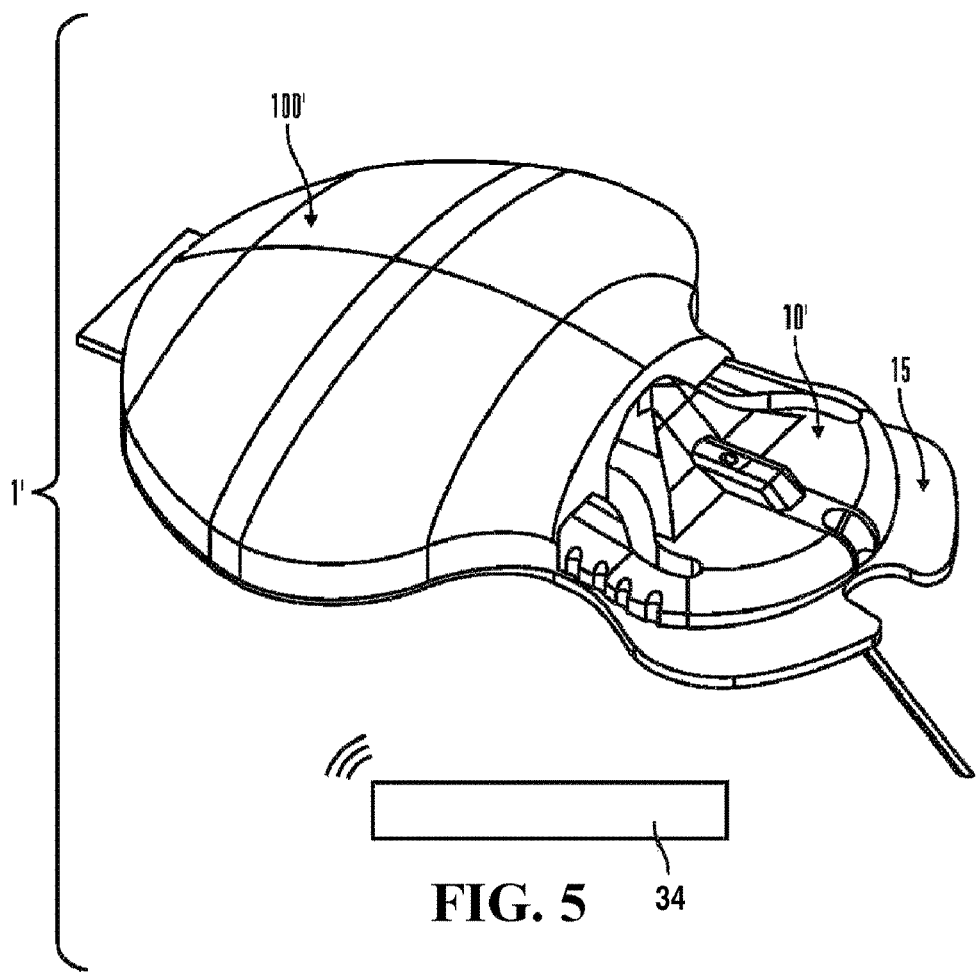
FIG. 5 is a perspective view illustrating another preferred embodiment of the subcutaneous sensor insertion set and telemetered characteristic monitor transmitter device when mated together in relation to the characteristic monitor system.
Figure 6:
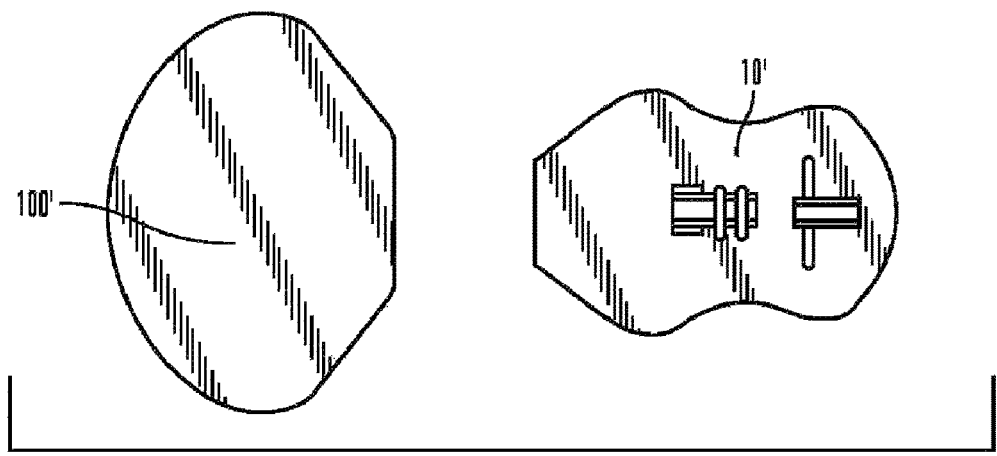
FIG. 6 is a top view of the subcutaneous sensor insertion set and telemetered characteristic monitor transmitter device when separated.

As shown in FIGS. 3(a)-(b), the telemetered characteristic monitor transmitter 30 is coupled to a sensor set 28 by a sensor cable 32. In alternative embodiments, the cable 32 may be omitted, and the telemetered characteristic monitor transmitter 30 may include an appropriate connector for direct connection to the connector portion 26 of the sensor set 28 or the sensor set 28 may be modified to have the connector portion 26 positioned at a different location. For example, FIGS. 5 and 6 show a possible alternative embodiment where characteristic monitor transmitter 100' and the sensor set 10' can be modified to allow a side-by side direct connection between the characteristic monitor transmitter 100' and the sensor set 10' such that the characteristic monitor transmitter 100' is detachable from the sensor set 10', as seen in FIG. 6. An adhesive 15 is used to attach the sensor set 10' to the user, and can also support the characteristic monitor transmitter 100'. Another possible embodiment (not shown) can modify the top of the sensor set 10' to facilitate placement of the telemetered characteristic monitor transmitter 100' over the sensor set 10'.

Figure 7:
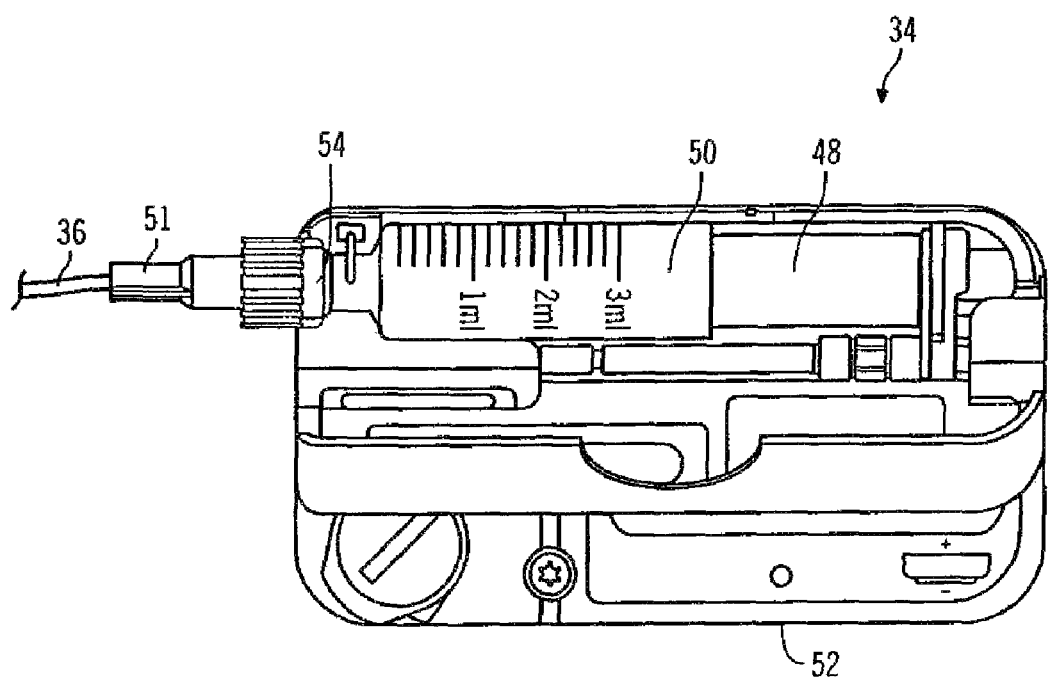
FIG. 7 is a top view of an infusion device with a reservoir door in the open position, for use in an embodiment of the present invention.
Figure 8:
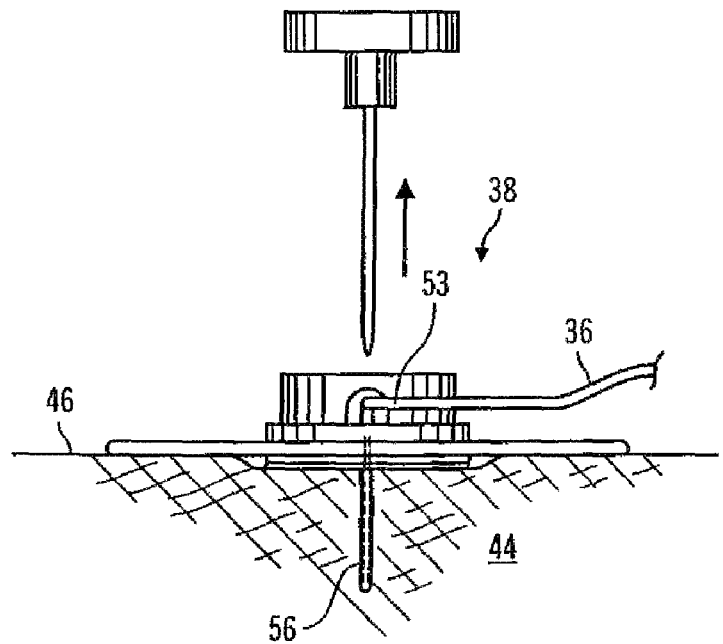
FIG. 8 is a side view of an infusion set with the insertion needle pulled out, for use in an embodiment of the present invention.

The controller 12 processes the digital sensor values Dsig and generates commands 22 for the infusion device 34. Preferably, the infusion device 34 responds to the commands 22 and actuates a plunger 48 that forces insulin 24 out of a reservoir 50 located inside the infusion device 34, as shown in FIG. 7. In particular embodiments, a connector tip 54 of the reservoir 50 extends through the infusion device housing 52 and a first end 51 of the infusion tube 36 is attached to the connector tip 54. A second end 53 of the infusion tube 36 connects to the infusion set 38. Insulin 24 is forced through the infusion tube 36 into the infusion set 38 and into the body 16. The infusion set 38 is adhesively attached to the user's skin 46, as shown in FIG. 8. As part of the infusion set 38, a cannula 56 extends through the skin 46 and terminates in the subcutaneous tissue 44 completing fluid communication between the reservoir 50 and the subcutaneous tissue 44 of the user's body 16.

In alternative embodiments, the closed-loop/semi-closed loop system can be a part of a hospital-based glucose management system. Given that insulin therapy during intensive care has been shown to dramatically improve wound healing, reduce blood stream infections, renal failure, and polyneuropathy mortality, irrespective of whether subjects previously had diabetes (See Van den Berghe G. et al. NEJM 345: 1359-67, 2001, which is incorporated by reference herein), the present invention can be used in this hospital setting to control the blood glucose level of a patient in intensive care. In these alternative embodiments, since an IV hookup is typically implanted into a patient's arm while the patient is in an intensive care setting (e.g. ICU), a closed loop glucose control can be established which piggy-backs off the existing IV connection. Thus, in a hospital based system, intravenous (IV) catheters which are directly connected to a patient vascular system for purposes of quickly delivering IV fluids, can also be used to facilitate blood sampling and direct infusion of substances (e.g. insulin, anticoagulants) into the intra-vascular space. Moreover, glucose sensors may be inserted through the IV line to give real-time glucose levels from the blood stream. Therefore, depending on the type of hospital based system, the alternative embodiments would not necessarily need the described system components such as the sensor 26, the sensor set 28, the telemetered characteristic monitor transmitter 30, the sensor cable 32, the infusion tube 36, and the infusion set 38 as described in the preferred embodiments. Instead, standard blood glucose meters or vascular glucose sensors as described in co-pending patent application entitled "Multi-lumen Catheter," filed Dec. 30, 2002, Ser. No. 10/331, 949, which is incorporated herein in its entirety by reference, can be used to provide the blood glucose values to the infusion pump control and the existing IV connection can be used to administer the insulin to the patient.

Figure 9A:
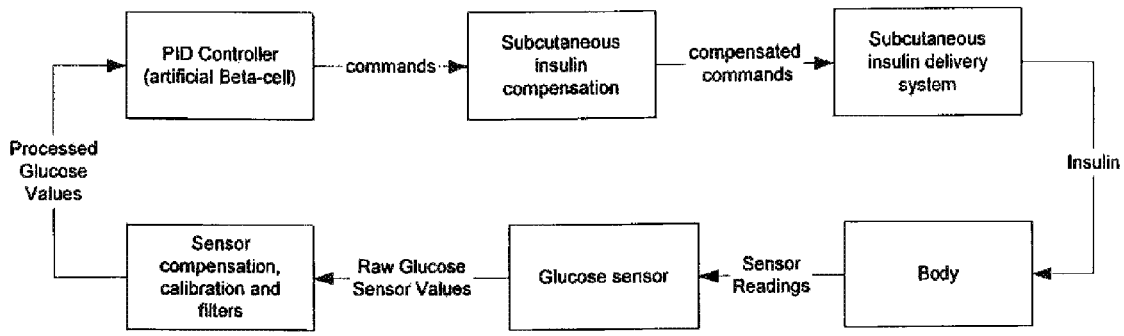
FIGS. 9 (a) and (b) are block diagrams of a closed loop glucose control system in accordance with embodiments of the present invention.
Figure 9B:
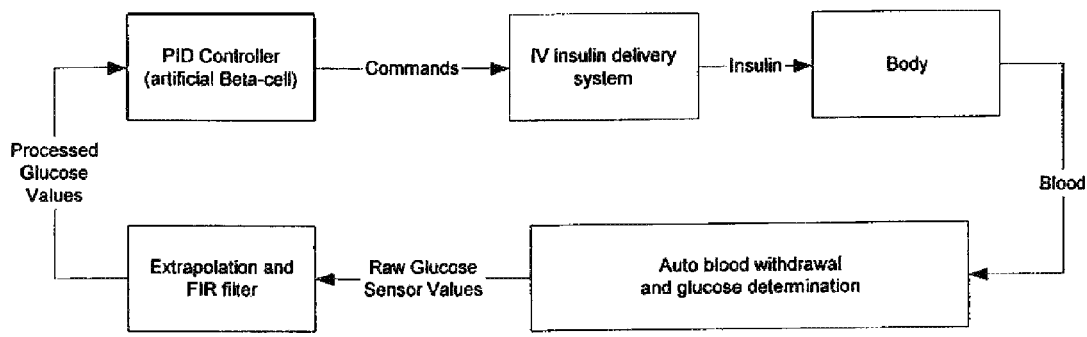
Figure 10:
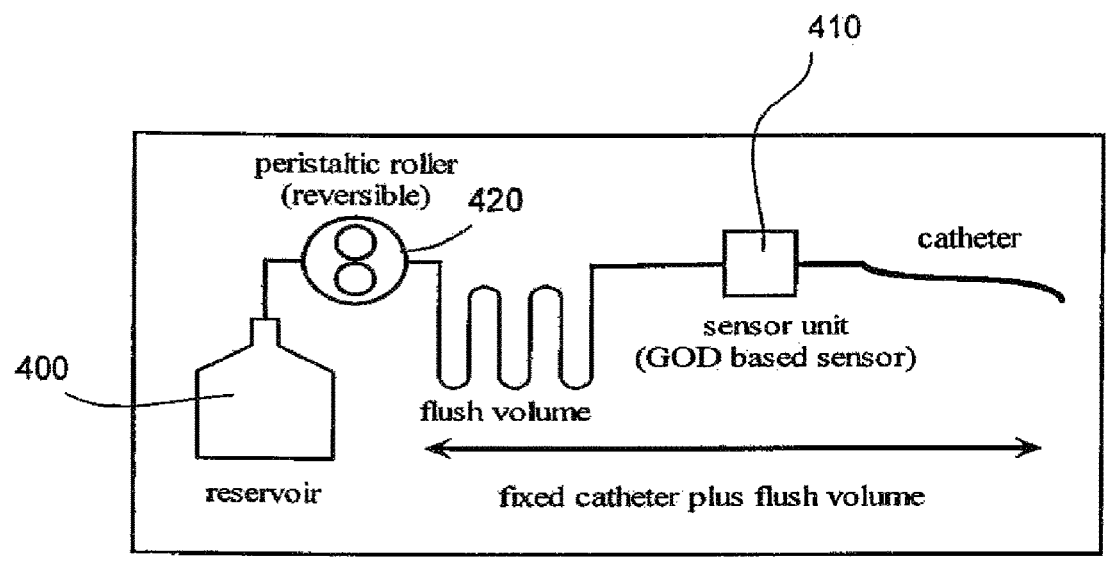
FIG. 10 is a block diagram of auto blood withdrawal and return in accordance with an embodiment of the present invention.

It is important to appreciate that numerous combinations of devices in the hospital-based system can be used with the closed loop controller of the present invention. For example, as described in FIG. 9b compared to a subcutaneous sensor system in FIG. 9a, an auto blood glucose/intravenous insulin infusion system can automatically withdraw and analyze blood for glucose concentration at fixed intervals (preferably 5-20 minutes), extrapolate the blood glucose values at a more frequent interval (preferably 1 minute), and use the extrapolated signal for calculating an iv-insulin infusion according to the controller described below. The modified auto blood glucose/intravenous insulin infusion system would eliminate the need for subcutaneous sensor compensation and subcutaneous insulin compensation which would be required with a subcutaneous sensor system (as described below when discussing the delay problems inherent in a subcutaneous sensor system). The automatic withdrawal of blood, and subsequent glucose determination can be accomplished with existing technology (e.g. VIA or Biostator like blood glucose analyzer) or by the system described in FIG. 10. The system in FIG. 10 uses a peristaltic pump 420 to withdraw blood across an amperometric sensor 410 (the same technology as used in sensor 26) and then return the blood with added flush (0.5 to 1.0 ml) from the reservoir 400. The flush can consist of any makeup of saline, heparin, glucose solution and/or the like. If the blood samples are obtained at intervals longer than 1 minute but less than 20 minutes, the blood glucose determinations can be extrapolated on a minute-to-minute basis with extrapolation based on the present (n) and previous values (n−1) to work with the logic of the controller as described in detail below. For blood samples obtained at intervals greater than 20 minutes, a zero-order-hold would be used for the extrapolation. Based on these blood glucose values, the infusion device can administer insulin based on the closed loop controller described in greater detail below.

In other modifications to the system, a manual blood glucose/intravenous insulin infusion system can be used where frequent manual entry of blood glucose values from a standard blood glucose meter (e.g. YSI, Beckman, etc) and extrapolate the values at more frequent intervals (preferably 1 min) to create a surrogate signal for calculating IV-insulin infusion. Alternatively, a sensor blood glucose/intravenous insulin infusion system can use a continuous glucose sensor (e.g. vascular, subcutaneous, etc.) for frequent blood glucose determination. Moreover, the insulin infusion can be administered subcutaneously rather than intravenously in any one of the previous examples according to the controller described below.

In still further alternative embodiments, the system components may be combined in a smaller or greater number of devices and/or the functions of each device may be allocated differently to suit the needs of the user.

Controller

Once the hardware for a closed loop system is configured, such as in the preferred embodiments described above, the affects of the hardware on a human body are determined by the controller. In preferred embodiments, the controller 12 is designed to model a pancreatic beta cell (β-cell). In other words, the controller 12 commands the infusion device 34 to release insulin 24 into the body 20 at a rate that causes the insulin concentration in the blood to follow a similar concentration profile as would be caused by fully functioning human β-cells responding to blood glucose concentrations in the body 20. Thus, the controller 22 is intended to emulate the in vivo insulin secretion pattern and to adjust this pattern to be consistent with in vivo β-cell adaptation. The in vivo β-cell response in subjects with normal glucose tolerance (NGT), with widely varying insulin sensitivity ($S_I$), is the optimal insulin response for the maintenance of glucose homeostasis. The biphasic insulin response of a β-cell can be modeled using components of a proportional, plus integral, plus derivative (PID) controller along with various filters. Description of a PID controller to emulate β-cells can be found in commonly assigned U.S. Pat. No. 6,558,351, which is incorporated with reference within in its entirety. In alternative embodiments, the controller may simply be the controller in an infusion pump that calculates the amount of insulin to be infused by knowing the insulin sensitivity/carbohydrate ratio of the individual, the target blood glucose level, amount of carbohydrates to be ingested and the current blood glucose level supplied by the sensor. An example of such a controller is described in commonly assigned U.S. Pat. No. 6,554,798 entitled "External Infusion Device with Remote Programming, Bolus Estimator and/or Vibration Alarm Capabilities," which is incorporated by reference within in its entirety.

Sensor Redundancy

Regardless of the controller used with the present system, closed loop/semi-closed loop algorithms for insulin delivery rely on a continuous glucose sensor to drive a control algorithm that determines the optimal insulin dose to administer through a pump delivery mechanism. Therefore sensor reliability and fault detection and handling are crucial to the dependability and safety of such an application. It is therefore desirable to have an assessment mechanism that can evaluate the sensor signal fidelity and initiate the appropriate action following detection of a sensor failure. In the event a fault is detected a request for sensor replacements should be initiated and a temporary suspension of insulin delivery or control should switch to a fixed mode of operation with set basal patterns.

One method of identifying whether the sensor values are reliable involves the measure of other signals by the sensor that may provide information about the state of the sensor (such as voltage readings, impedance, etc). This approach has some merit, but we cannot assure that we always know the sensor is accurate. Another possibility to assure an accurate sensor reading is to use a dual or 3-up sensing system located in a single sensor site so that the sensors could be used to check one another. This approach has merit because the system would continue in closed-loop mode as long as the sensors were in agreement, and the likelihood of each sensor failing in the same way, or at the same time is supposedly small. However, there exists the possibility that an interferon affects all sensors the same way, or the sensor insertion site is affected so that all sensors misread the glucose in a similar fashion. Thus, several situations can arise were two functioning sensors produce dissimilar outputs, or two dysfunctional sensors could present similar outputs that are credible of a person's glucose state. Therefore, even this technique may have a potential failure mode.

Consequently, the subject of this present invention relates to the use of sensor redundancy, where the sensing method and/or sensor location are different from one another. For example, in one embodiment, two subcutaneous sensors located at different sites would assure that the potential for common effects due to sensor location or interferences is negligible. However, alternative sites may generate different physiological delays that could result from skin temperature or pressure variance at the measuring site. For example, when additional pressure is applied to one of the sites due to sleep posture, the readings may vary. Moreover, two identical sensors who should exhibit the same readings can exhibit varying time lags, sensitivities and offsets leading to confusing signals. Thus, in preferred embodiments, sensors using different technology are placed in different body fluids, e.g. one sensor in subcutaneous tissue and one in blood. Therefore, although the previous description described various types of electro-enzymatic sensors, the system will use other types of sensors, such as chemical based, optical based or the like. For example other types of sensors are described in the following references: U.S. Provisional Application Ser. No. 60/007,515 to Van Antwerp et al. and entitled "Minimally Invasive Chemically Amplified Optical Glucose Sensor"; U.S. Pat. No. 6,011,984 issued Jan. 4, 2000 to Van Antwerp et al. and entitled "Detection of Biological Molecules Using Chemical Amplification"; and U.S. Pat. No. 6,766,183 issued Jul. 20, 2004 to Walsh et al. and entitled "Long Wave Flourophore Sensor Compounds and Other Fluorescent Sensor Compounds in Polymers", all of which are herein incorporated by reference. Other compounds using Donor Acceptor fluorescent techniques may be used, such as disclosed in U.S. Pat. No. 5,628,310 issued May 13, 1997 to Rao et al. and entitled "Method and Apparatus to Perform Trans-cutaeous Analyte Monitoring"; U.S. Pat. No. 5,342,789 issued Aug. 30, 1994 to Chick et al. and entitled "Method and Device for Detecting and Quantifying Glucose in body Fluids"; and U.S. Pat. No. 5,246,867 issued Sep. 21, 1993 to Lakowicz et al. and entitled "Determination and Quantification of Saccharides by Luminescent Lifetimes and Energy Transfer", all of which are herein incorporated by reference. The bottom line is that, use of two different types of sensors at two different locations, may offer the ideal redundancy needed to assure failsafe performance of the system that relies heavily on accurate sensor readings.

Challenges to Sensor Redundancy

Figure 12A:
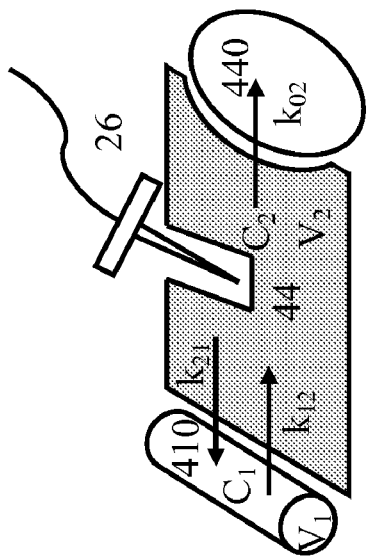
FIG. 12(a) is a model describing the relationship between glucose in interstitial fluid and plasma glucose in accordance with an embodiment of the present invention.
Figure 12B:
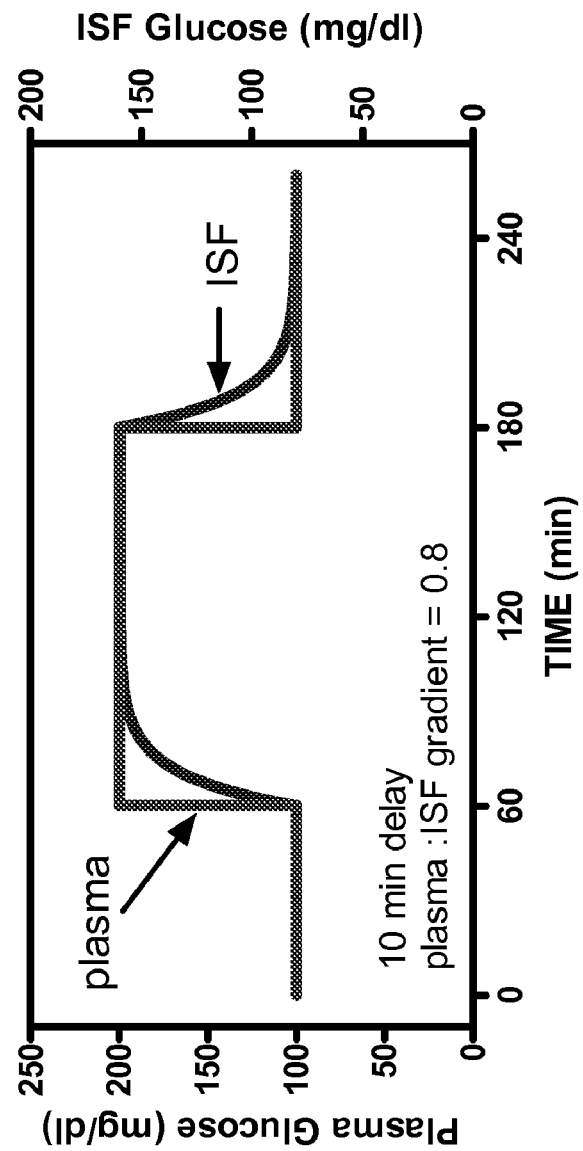
FIG. 12(b) is a plot of a plasma glucose step in comparison with the resulting interstitial fluid glucose concentration.

However, different sensor technologies and different measurement fluids are known to have significantly varying time lags. For example, the complexity of the problem can be seen with a subcutaneous glucose sensor 26. As described with respect to FIG. 11, a physiological delay 422 is due to the time required for glucose to move between blood plasma 420 and interstitial fluid (ISF). The delay is represented by the circled double headed arrow 422 in FIG. 11. Generally, as discussed above, the sensor 26 is inserted into the subcutaneous tissue 44 of the body 20 and the electrodes 42 near the tip of the sensor 40 are in contact with interstitial fluid (ISF). But the desired parameter to be measured is the concentration of blood glucose. Glucose is carried throughout the body in blood plasma 420. Through the process of diffusion, glucose moves from the blood plasma 420 into the ISF of the subcutaneous tissue 44 and vice versa. As the blood glucose level 18 changes so does the glucose level in the ISF. But the glucose level in the ISF lags behind the blood glucose level 18 due to the time required for the body to achieve glucose concentration equilibrium between the blood plasma 420 and the ISF. Studies show the glucose lag times between blood plasma 420 and ISF vary between 0 to 30 minutes. Some parameters that may affect the glucose lag time between blood plasma 420 and ISF are the individual's metabolism, the current blood glucose level, whether the glucose level is rising, or falling, or the like. A model illustrated in FIG. 12*a* has been created to describe this dynamic relationship between ISF and plasma glucose. This model is based on the assumption that the capillary 410 separating plasma 420 and ISF in the subcutaneous tissue 44 compartments creates a resistance to glucose diffusion into the ISF space (i.e. subcutaneous space). Glucose is cleared from the ISF space 44 into Fat/Muscle Cells 440 by a rate proportional to the concentration of glucose in that compartment. This mathematical relationship is described by the following mass balance equation:

$$\frac{dC_2}{dt} = -(k_{02} + k_{12})C_2 + k_{21}\frac{V_1}{V_2}C_1 \tag{1}$$

where the rate of glucose clearance from the subcutaneous tissue has a constant uptake rate of $k_{02}$, and constant glucose diffusion rates between the plasma and subcutaneous tissue $k_{12}$ and $k_{21}$. The plasma 420 and ISF in the subcutaneous tissue 44 have glucose concentrations $C_1$ and $C_2$ with corresponding volumes $V_1$ and $V_2$ respectively. The plasma 120 to ISF 130 time constant and gradient can be expressed as:

$$\frac{C_2}{C_1} = \frac{k_{21}}{k_{12} + k_{02}} \cdot \frac{V_1}{V_2}, \tag{2}$$

$$\tau = \frac{1}{k_{12} + k_{02}}$$

where time constant $\tau$ is the time delay between plasma and ISF glucose. Equation (2) assumes steady state conditions where the steady state glucose concentration in the ISF compartment ($C_2$) is dependent upon the rate of glucose clearance from this compartment ($k_{02}$) and the rate of glucose diffusion to the compartment ($k_{12}$ and $k_{21}$). All rate parameters are assumed constant therefore the time lag between ISF and plasma glucose concentration is also constant, as is the gradient. A theoretical plasma glucose step response is then illustrated in FIG. 12*b* with the resulting ISF glucose concentration superimposed with a gradient of 0.8 and first order time lag of 10 minutes. It takes approximately 50 minutes or 5 time constants for the transient response from ISF glucose concentration to completely equilibrate. As illustrated in FIG. 12*a* plasma glucose can be estimated from a measurement of ISF glucose through an electrochemical sensor 28. A low current in the nA range is measured through an electrochemical reaction which is considered to be proportional to ISF glucose. The electrochemical sensor will generate a similar transient like transport delay in addition to this physiologic delay.

Figure 11:
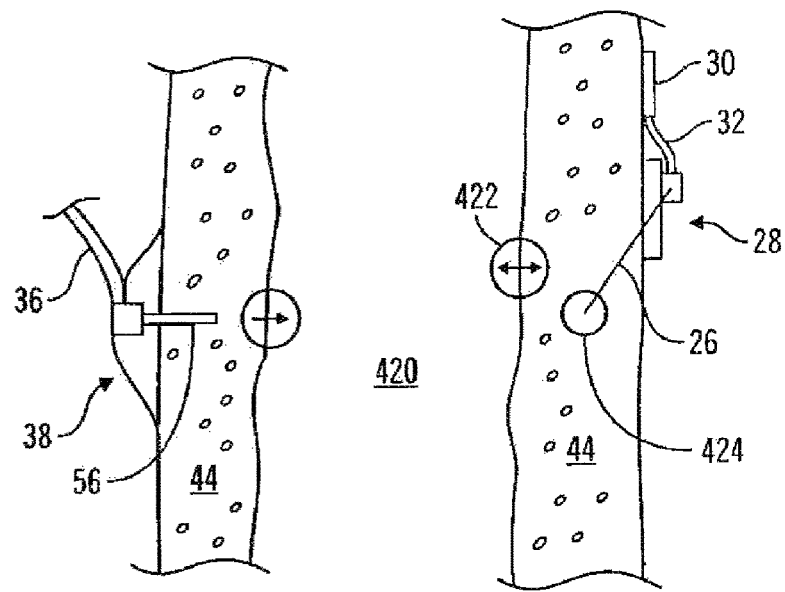
FIG. 11 is a cross-sectional view of a sensor set and an infusion set attached to the body in accordance with an embodiment of the present invention.

In addition, a chemical reaction delay 424 is also introduced by the sensor response time, represented by the circle 424 surrounding the tip of the sensor 26 in FIG. 11. The sensor electrodes 42 are coated with protective membranes that keep the electrodes 42 wetted with ISF, attenuate the glucose concentration, and reduce glucose concentration fluctuations on the electrode surface. As glucose levels change, the protective membranes slow the rate of glucose exchange between the ISF and the electrode surface. In addition, there is a chemical reaction delay simply due to the reaction time for glucose to react with glucose oxidase GOX to generate hydrogen peroxide, and the reaction time for a secondary reaction, the reduction of hydrogen peroxide to water, oxygen and free electrons. Although this sensor delay can be identified, different site anomalies could create even greater time lag variance. This sensor lag time can also vary slightly between manufacturing batches and often have different offsets. Microdialysis sensors are known to have a much greater delay due to the long diffusion process across the dialysis membrane. Sensors utilizing florescent and infrared optics again have different sets of characteristics.

There are also processing delays as the analog sensor signal Isig is converted to digital sensor values Dsig. In preferred embodiments, the analog sensor signal Isig is integrated over one-minute intervals and then converted to a number of counts. In essence this one-minute integration creates a delay of 30 seconds. In particular embodiments, the one-minute values are averaged into 5-minute values before they are sent to the controller. The resulting average delay is two and one half minutes. In alternative embodiments, longer or shorter integration times are used resulting in longer or shorter delay times. In other embodiments the analog sensor signal current Isig is continuously converted to an analog voltage Vsig and a A/D converter samples the voltage Vsig every 10 seconds. Then six 10-second values are pre-filtered and averaged to create a one-minute value. Finally, five 1-minute values are filtered and then averaged creating a five-minute value resulting in an average delay of two and one half minutes. Other embodiments use other electrical components or other sampling rates and result in other delay periods.

Solution to Prior Obstacles when Using Redundant Sensors

Given the present difficulties of having a single sensor work effectively to give reliable sensor readings, the addition of additional sensors have not been considered in the prior art. However, the present invention devises a method and system where two different sensors with varying site differences and sensor variances can still be used to model a transfer function difference between each other that can help corroborate each other's readings and identify each other's failures. This transfer function encompasses differences in sensing site characteristics and time varying intrinsic sensor dynamics. These models enable each sensor output to be predicted based on the other sensor signal. Although the preferred embodiment envisions two different types of sensors in different sites, the algorithm described below can function with two similar sensors sampling the same space or two sensors of completely different technologies sampling different fluid e.g. plasma, whole blood or ISF. The approach adjusts a set of filter coefficients based on the difference in each real-time sensor reading. As this is a data based approach it has the benefit of not requiring much information about the sensor, sensor site or sensor characteristics.

Figure 13:
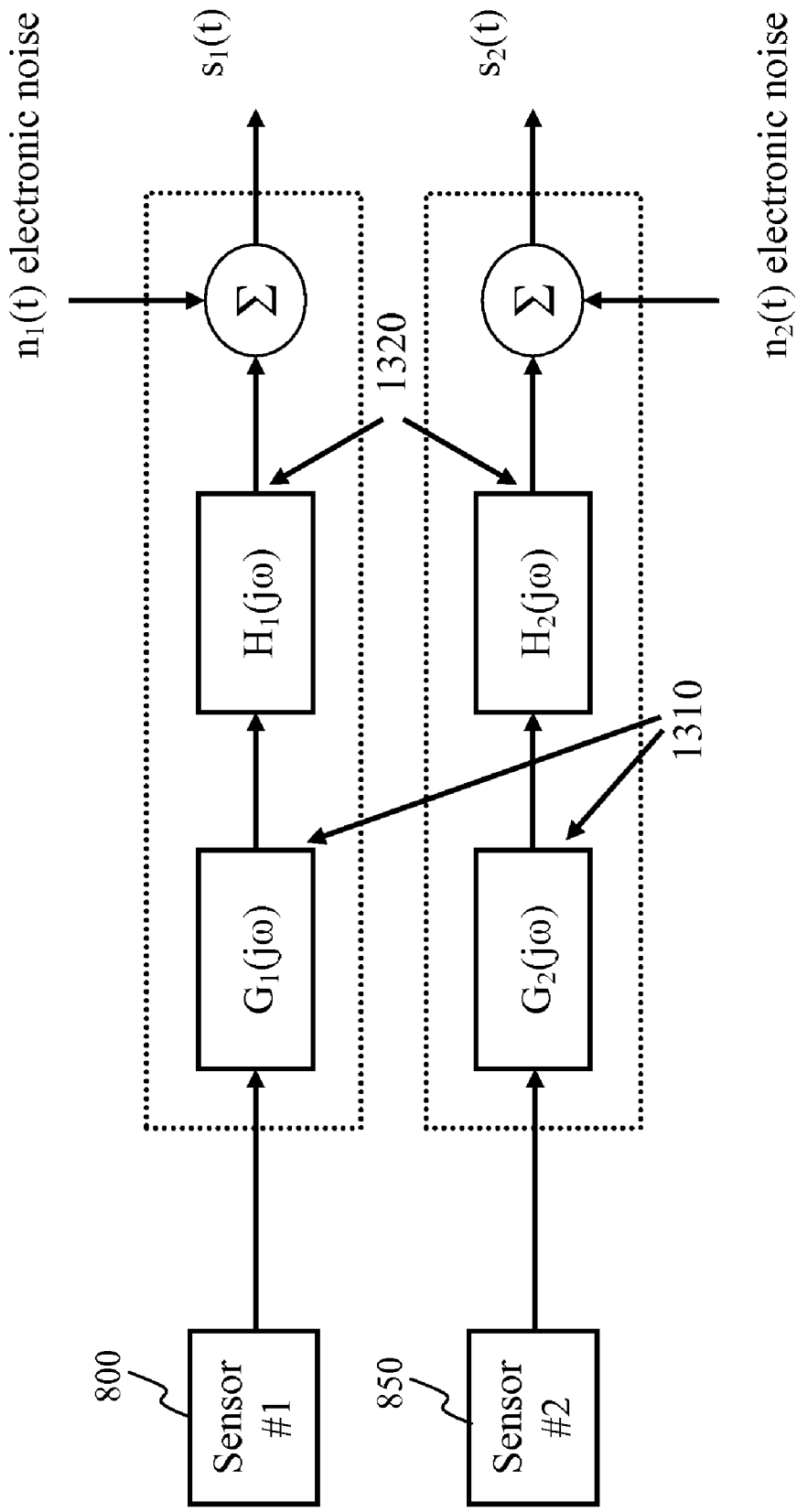
FIG. 13 illustrates a block diagram of two glucose sensors simultaneously attached to the body at different locations in accordance with an embodiment of the present invention.
Figure 14:
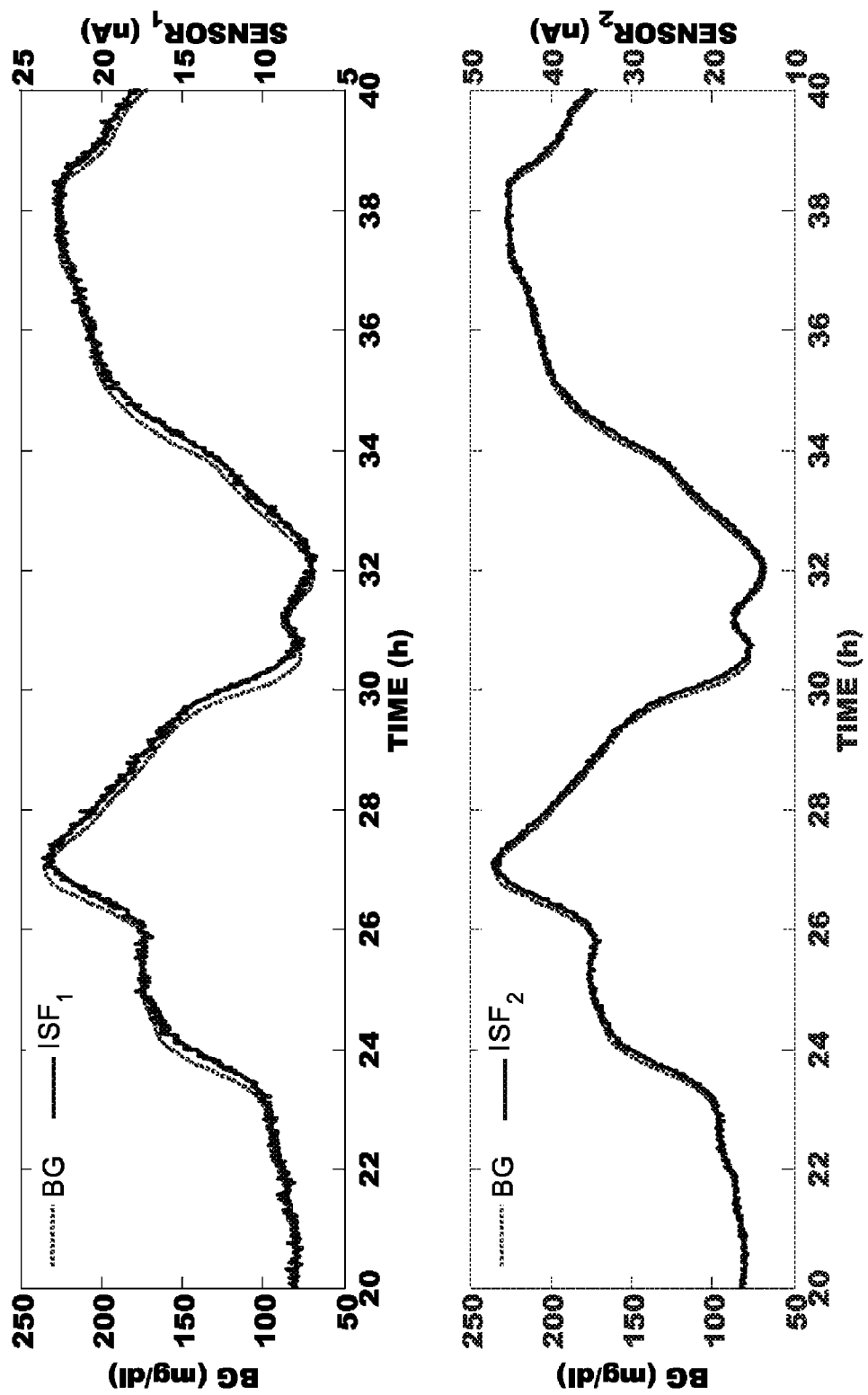
FIG. 14 is a plot of the two glucose sensors of FIG. 13 over time compared to a reference blood glucose value in accordance with embodiments of the present invention.

The block diagram illustrated in FIG. 13 describes two glucose sensors 800 and 850 simultaneously attached to the body at different locations. For the specific example of FIG. 13, two sensors 800 and 850 are the same type inserted in the subcutaneous tissue of (1) the arm and (2) the abdomen to measure glucose in the interstitial fluid. The values are compared to a reference blood glucose value to see actual differences in delay and noise. However, in other examples, the sensors 800 and 850 can be the same type or two different type of sensors. FIG. 13 shows the sources of lag in glucose measurement in both sensors 800 and 850 where the digitized sensor signal contains a combination of first order lags and gradient effects. The first lag and gradient effect 1310 encountered in this process originates from the measurement site and the second lag and gradient effect 1320 is a transport lag intrinsic to all glucose sensors. As this algorithm is data driven it adapts automatically to either characteristic. The first sensor site is characterized by a first order filter $G_1(j\omega)$ which has the effect of creating a time lag of some finite duration and signal attenuation similar to the effect illustrated in FIG. 12B. This delay is proportional to the rate of glucose diffusion into the measuring space. Following this delay and attenuation the signal will be further delayed and attenuated by sensor transport lags and the diffusion process of the sensor type characterized by a first order filter $H_1(j\omega)$. Cascaded together both filters have a second order effect. The second sensor site is characterized by the first order filter $G_2(j\omega)$ and the second sensor is characterized by $H_2(j\omega)$, which have similar characteristics to the first sensor and site but with differing magnitude and delay. Further to this combined effect, all sensors contain some degree of electronic noise $n_1(t)$ and $n_2(t)$. Two first order effects provide a second order frequency response the equivalent to having two cascaded filters. In an example, the first site $G_1(j\omega)$ creates a gradient of 0.1 and a time lag of 10 minutes. This is followed by an additional lag of 2 minutes with unity gradient from the first sensor $H_1(j\omega)$. The resultant sensor signal is $s_1(t)$ from the first sensor 800 which is a combination of these effects with white Gaussian noise added to simulate electronic noise. The second site $G_2(j\omega)$ has a time lag of 5 minutes and gradient of 0.2. The sensor time lag $H_2(j\omega)$ is 1 minute with unity gradient. The second sensor signal $s_2(t)$ from the second sensor 850 has additive white noise of similar power. FIG. 14 traces sensor signals from both sensors 800 and 850. The signals at each processing stage are illustrated in FIG. 14 where it is obvious that the first trace has the greatest lag when comparing to the BG signal sampled from plasma. The second sensor signal $s_2(t)$ has twice the amplitude of the first sensor signal $s_1(t)$ but only half the time delay. Noise corruption is obvious from both traces.

Figure 15:
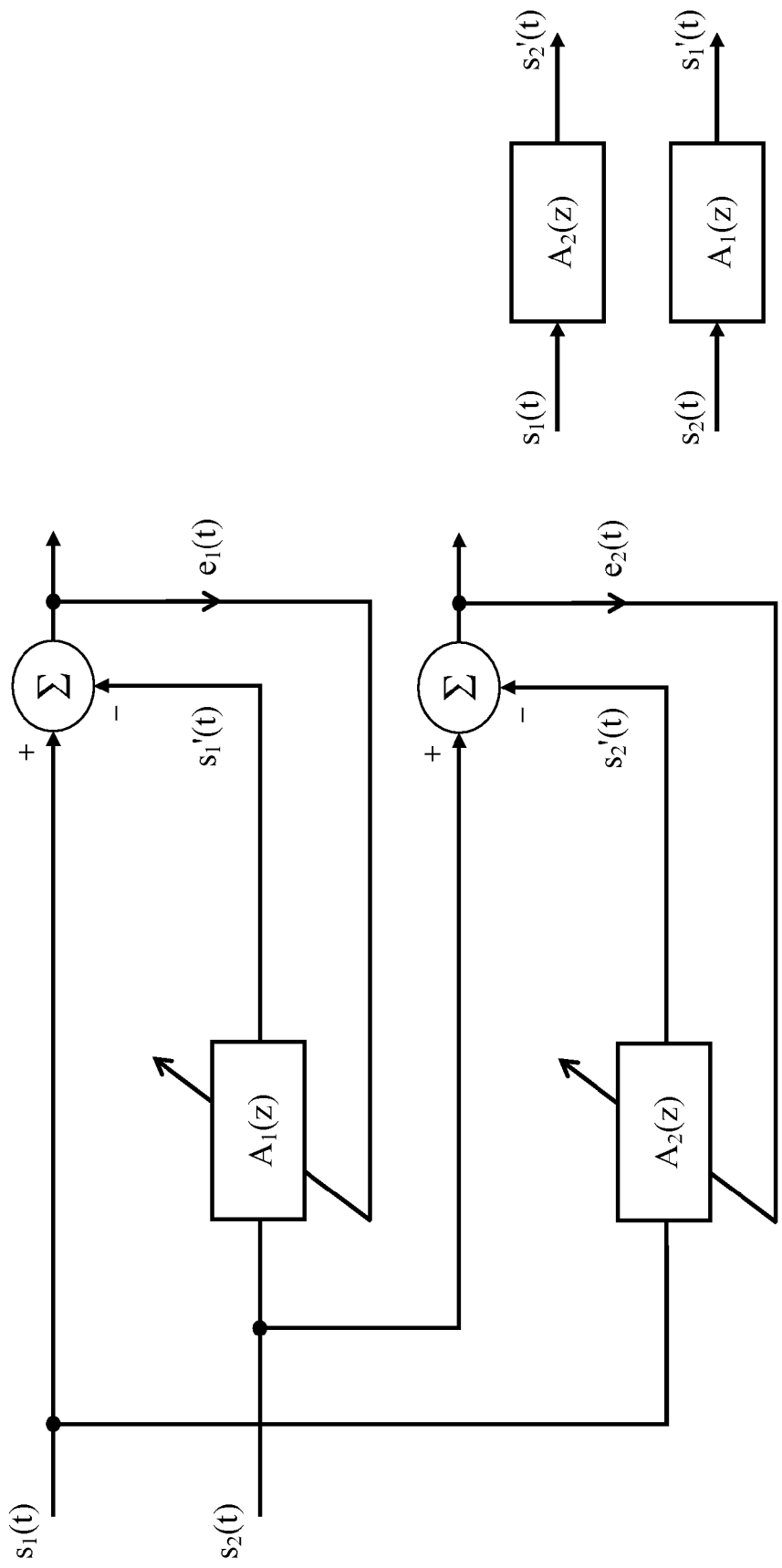
FIG. 15 describes the adaptive filter arrangement used to provide sensor corroboration and fault checking between the two sensors in accordance with embodiments of the present invention.

In order to evaluate sensor reliability, were a divergence between two filter residuals will indicate a possible fault in one or both sensors 800 and 850, the adaptive filter arrangement of FIG. 15 is used to perform system identification and tuning of two predictive filters. Following a sufficient training period, each predictive filter $A_1(z)$ and $A_2(z)$ can predict a sensor output using the other sensor as input. Either infinite impulse response (IIR) or finite impulse response (FIR) filters would suffice. The examples presented in this document use $32^{nd}$ order FIR filters where predictions are described by Equations 3 and 4:

$$s'_1(k) = \sum_{n=0}^{N-1} A_1(n) s_2(k-n) \quad (3)$$

$$s'_2(k) = \sum_{n=0}^{N-1} A_2(n) s_1(k-n) \quad (4)$$

In the above Equations adaptive filter coefficients $A_1$ and $A_2$ are continuously adjusted to match the combined response of site and sensor filters $G_1(j\omega) \cdot H_1(j\omega)$ and $G_2(j\omega) \cdot H_2(j\omega)$ which characterize the medium between the glucose and the acquired sensor signal. The primes denote a prediction value for sensor signals $s_1$ and $s_2$. During the tuning process errors are calculated from each filter output described by Equations 5 and 6, and are fed back to adapt the corresponding filter coefficients.

$$e_1(k) = s_1(k) - s_1'(k) \quad (5)$$

$$e_2(k) = s_2(k) - s_2'(k) \quad (6)$$

An adaptive algorithm is used to update the coefficients to best minimize this error. The adaptive tuning algorithm utilized in the preferred embodiment is a recursive least squares (RLS) algorithm which exponentially weights data to gradually remove the effects of old data and thus tracking varying characteristics slowly. This is particularly important as sensor characteristics can drift over time since sensitivities may vary, whether related directly to sensor stability or the body's natural reaction at the site by the wound healing process. Nonetheless this approach should compensate for changing characteristics with periodic update tuning of the filter coefficients. In alternative embodiments, other adaptive tuning algorithms can be used instead of the RLS algorithm ranging from the simplistic least means squares (LMS) algorithm to the more complicated Kalman filtering and the like.

Figure 16:
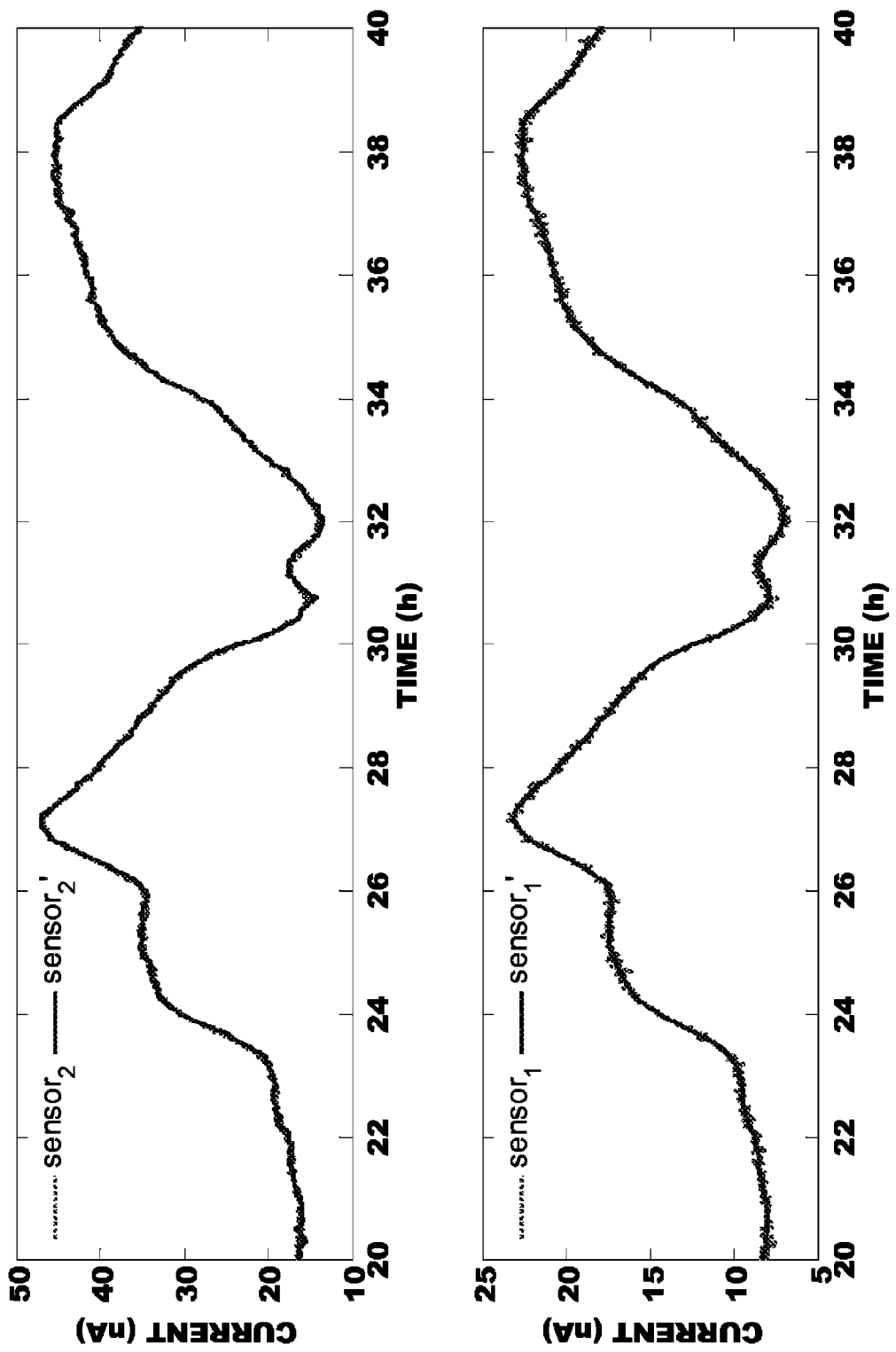
FIG. 16 is a plot of the unprocessed sensor signals with the corresponding prediction traces calculated with adaptive filters in accordance with embodiments of the present invention.
Figure 17:
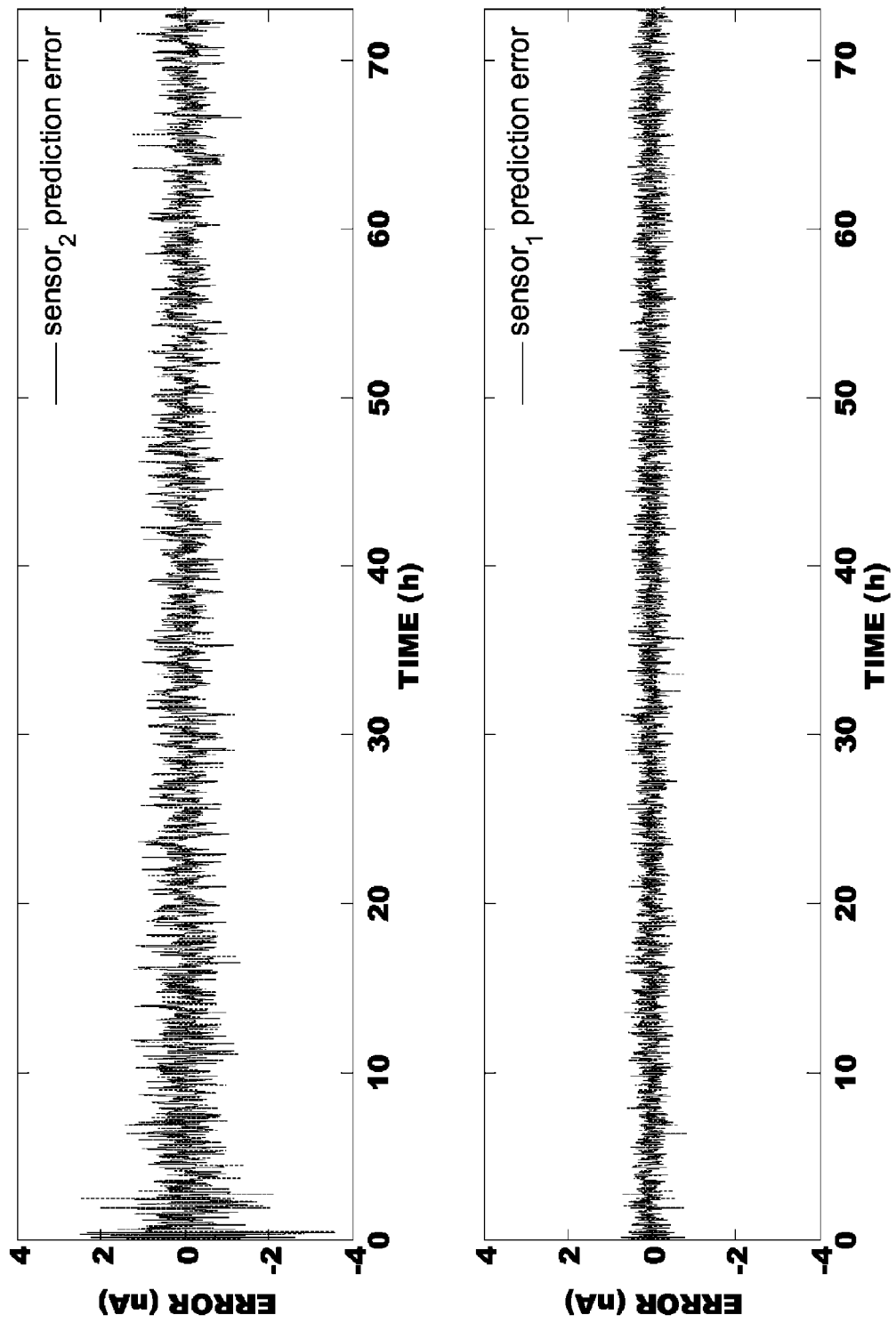
FIG. 17 is a plot of the performance of each prediction of the sensor values in accordance with embodiments of the present invention.
Figure 18:
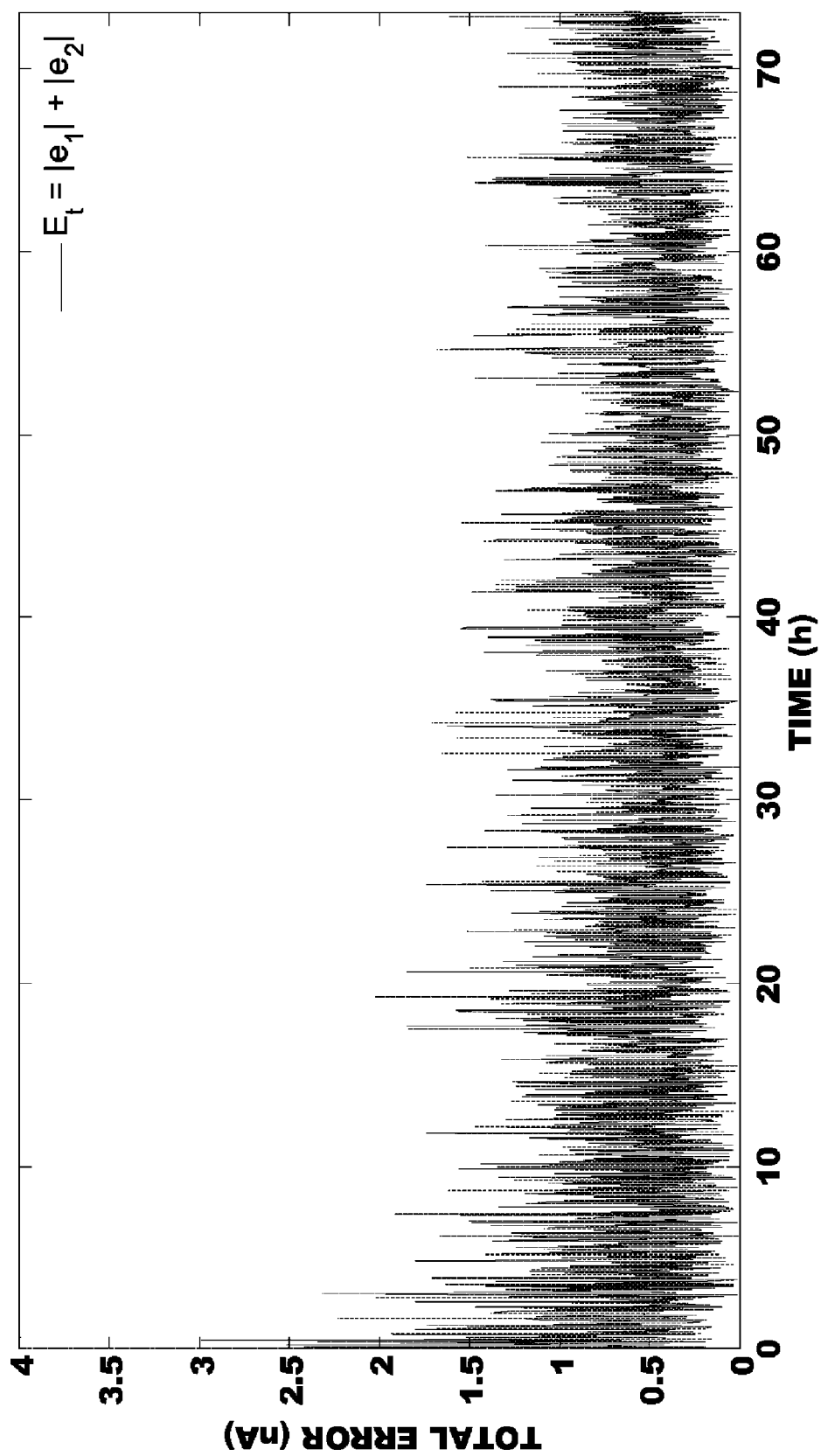
FIG. 18 is a plot of the fault detection in accordance with embodiments of the present invention.

The unprocessed sensor signals are illustrated in FIG. 16 with the corresponding prediction traces calculated with adaptive filters following a short tuning duration. The first trace of FIG. 16 shows the second sensor trace $s_2(t)$ and the sensor prediction $s_2'(t)$ calculated by applying the first sensor trace $s_1(t)$ to filter $A_2(z)$. Clearly time delay and gain has been accurately accounted for with a small amount of noise still present in the processed signal. The second trace of FIG. 16 shows the first sensor trace $s_1(t)$ and its corresponding prediction $s_1'(t)$ by applying the second sensor signal $s_2(t)$ to filter $A_1(z)$. It can be seen that the prediction not only corrects for gain and time lag but also predicts the sensor signal with an improved signal-to-noise (SNR) ratio. This has additional benefit to sensor fault detection were based on a secondary signal sensor noise can be filtered from the primary sensor signal without incurring an additional delay. This is significantly beneficial for closed-loop algorithms in particular that make fast dosing decisions. The performance of each prediction is illustrated in FIG. 17 where the first trace is the error in predicting the second sensor based on the first sensor. The second trace shows the error in predicting the first sensor using the second sensor as input. Evidently the tuning process is efficient approximately reaching sufficient performance in less than 2.5 hours. Fault detection as illustrated in FIG. 18 is based on a combined error calculation expressed by Equation 7 where a combined error of $E_t < 2$ nA indicates that both sensors are functioning correctly and no fault action should be taken. An alarm should alert if this threshold is exceeded and the logic will enter a fault handling mode (as described in detail below).

$$E_t(t)=|e_1(t)|+|e_2(t)| \quad (7)$$

Under normal working conditions (no fault, combined error $E_t$<2 nA) the sensor output with the minimum error expressed by Equation (8) should be used to drive the control algorithm for an output y for the $n^{th}$ sample. This will indicate the sensor with the least noise.

$$y(n) = \begin{cases} s_1(n), & |e_1(n)| \le |e_2(n)| \\ s_2(n), & |e_1(n)| > |e_2(n)| \end{cases} \quad (8)$$

Figure 19:
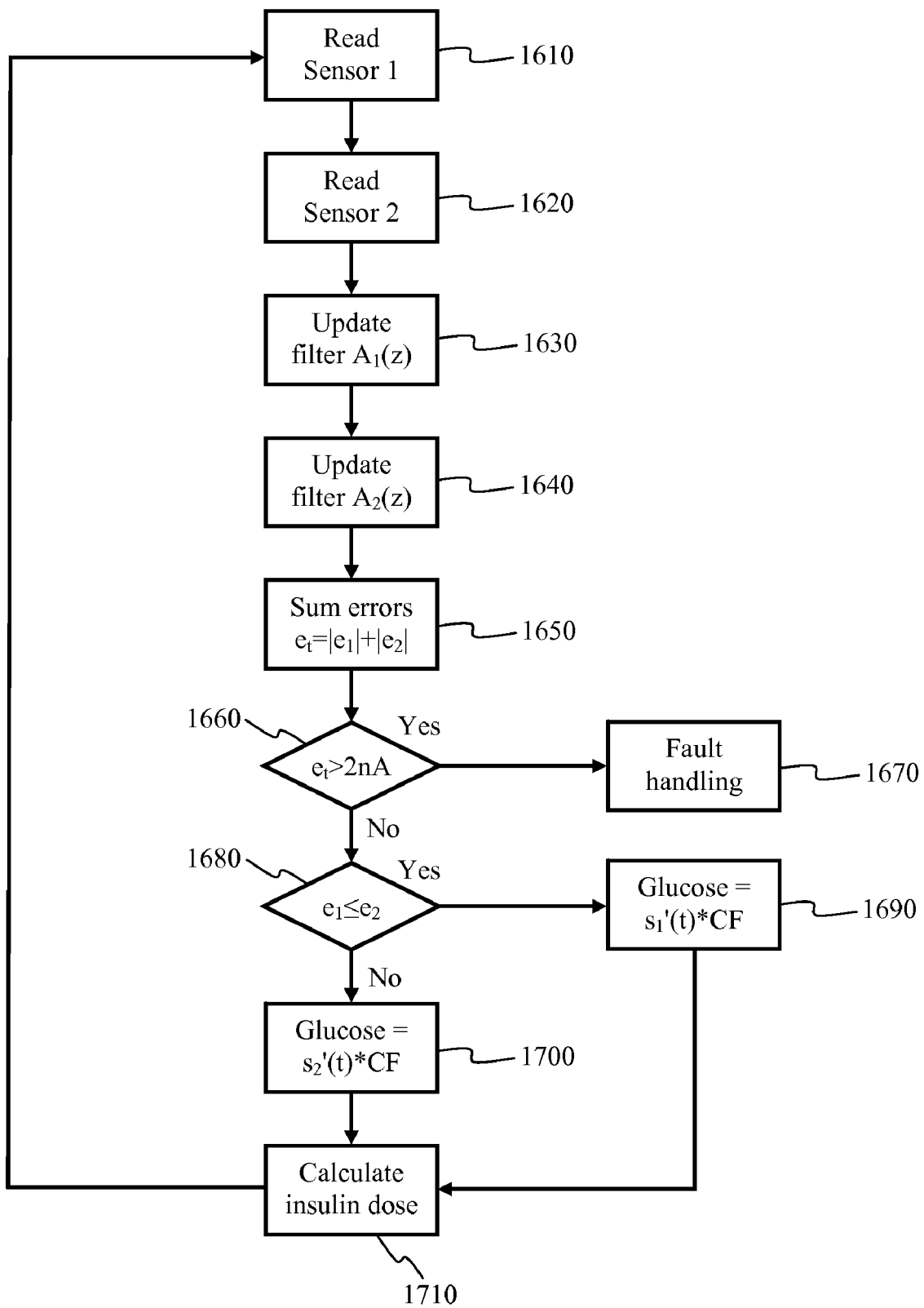
FIG. 19 is a flowchart illustrating the steps used by the adaptive filter arrangement of FIG. 15 in accordance with embodiments of the present invention.

FIG. 19 is a flowchart explaining the steps used by the adaptive filter arrangement of FIG. 15 in accordance with embodiments of the present invention. The algorithm starts at block 1610 where the controller 12 receives sensor values $s_1(t)$ from the first sensor 800. At block 1620, the controller 12 receives sensor values $s_2(t)$ from second sensor 850. At block 1630, the first predictive filter $A_1(z)$ begins to predict the value $s_1'(t)$ of the first sensor 850 using the sensor values $s_2(t)$. Similarly, at block 1640, the second predictive filter $A_2(z)$ begins to predict the value $s_2'(t)$ of the second sensor 800 using the sensor values $s_1(t)$. At block 1650, the difference between the first sensor value $s_1(t)$ and the first predicted sensor value $s_1'(t)$ is calculated as $e_1(t)$ and the difference between the second sensor value $s_2(t)$ and the second predicted sensor value $s_2'(t)$ is calculated as $e_2(t)$. The total error $E_t$ is then calculated by adding the absolute values of $e_1(t)$ and $e_2(t)$. At block 1660, the total error $E_t$ is compared to a threshold value. In the preferred embodiment, the threshold is set at 2 nA, but the value can be increased or decreased based on the system's tolerance for error. If the total error $E_t$ is greater than the threshold, the algorithm will indicate a sensor failure and go into a fault handling mode at block 1670. The fault handling mode will be described in detail with respect to FIG. 20. Otherwise, if the total error $E_t$ is less than or equal to the threshold, then at block 1680, the logic will determine which sensor has the least amount of noise. If the first sensor is showing less noise, then the logic goes to block 1690 where the predicted sensor value for the first sensor $s_1'(t)$ is used to calculate the blood glucose value of the individual (i.e. $s_1'(t)$* CF), where CF is a calibration factor used to calibrate the sensor signal to provide a BG value. On the other hand, if the second sensor is showing less noise, the logic goes to block 1700 where the predicted sensor value for the second sensor $s_2'(t)$ is used to calculate the blood glucose value of the individual (i.e. $s_2'(t)$*CF). In alternative embodiments, the actual sensor values of the sensor will be used to calculate the blood glucose values rather than the predicted sensor values. Regardless, based on the selected glucose sensor value, the controller 12 can calculate the amount of insulin that should be administered at block 1710 using the selected glucose sensor value.

Figure 20:
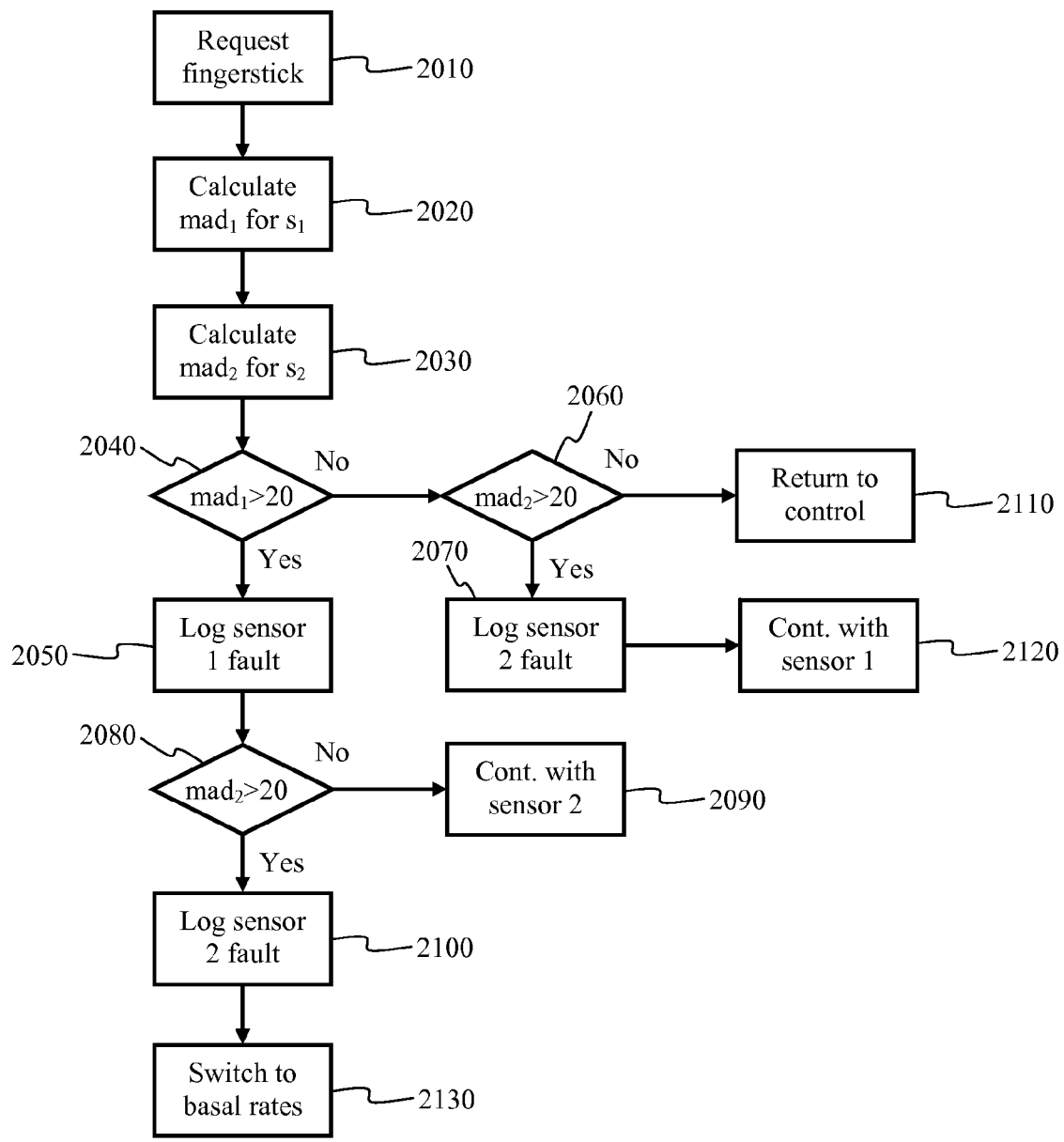
FIG. 20 is a flowchart illustrating the steps in the fault handling process of FIG. 16 in accordance with embodiments of the present invention.

FIG. 20 is a flowchart explaining the steps in the fault handling process of FIG. 19 in accordance with embodiments of the present invention. Given the small likelihood that both sensors would fail at the same time, the fault handling process of FIG. 20 is used to determine which sensor is failing and should not be used further, and provides a temporary working solution until the faulty sensor can be replaced. The logic also provides a method to determine if both sensors are failing and determine that the closed-loop operation should immediately cease. The logic starts at block 2010 where an alarm would be triggered once the logic enters the fault handling mode. The alarm would include a request for a current meter value using the traditional finger prick method. The current meter value will be used as a current blood glucose value to compare against each sensor reading. At block 2020 and 2030, the mean absolute difference calculated as a percentage between the current blood glucose value and the first sensor 800 and the second sensor 850 will be calculated. The mean absolute difference can be calculated as follows:

$$mad_1 = 100*|CF \cdot s_1 - BG|/BG\%$$

$$mad_2 = 100*|CF \cdot s_2 - BG|/BG\%$$

At block 2040, the mean absolute difference for the first sensor 800 will be compared to a threshold value to determine if the blood glucose value returned by the first sensor 800 deviates too much from the current blood glucose value returned by the meter. In the preferred embodiment the threshold is set to a 20% difference. However, in alternative embodiments, the threshold can be set to a higher or lower value. If the threshold is exceeded, the logic at block 2050 will determine that first sensor 800 is faulty and report that the first sensor 800 is failing. After the first sensor 800 values are checked at block 2040, the second sensor 850 values are checked at blocks 2060 and 2080. At block 2060 and 2080, the mean absolute difference for the second sensor 850 will be compared to the same threshold value to determine if the blood glucose value returned by the second sensor 850 deviates too much from the current blood glucose value returned by the meter. If the threshold is exceeded, the logic at blocks 2070 and 2100 will determine that second sensor 850 is faulty and report that the first sensor 850 is failing. Depending on which sensors are determined to be failing, the logic defaults to four different possibilities. The first possibility is found at block 2110. If both sensors 800 and 850 are do not exceed the threshold (and thus, neither sensor is determined to be failing), the logic at block 2110 exits the fault handling mode and returns back to normal operation of FIG. 19. The second possibility is found at block 2120 where only the second sensor 850 is found to be failing. In this case, the logic of block 2120 will stop using the signals from the second sensor 850, and the closed loop system/semi-closed loop system will continue using only the sensor values from the first sensor 800 until the second sensor 850 can be replaced. Similarly, the third possibility is found at block 2090 where only the first sensor 800 is found to be failing. In this case, the logic of block 2090 will stop using the signals from the first sensor 800, and the closed loop system/semi-closed loop system will continue using only the sensor values from the second sensor 850 until the first sensor 800 can be replaced. The last possibility is found at block 2130, where both sensors are found to be failing and need replacement. If the logic of block 2130 is triggered a different insulin delivery strategy should be immediately adopted such as limiting the insulin delivery only to minimal basal amounts.

In an alternative embodiment, one sensor will act as the primary sensor, and the second sensor will act as a watchdog. In an example of this embodiment, the second sensor 850 will only be used to detect if the first sensor 800 is failing. If the total error $E_t$ exceeds the threshold at block 1660 of FIG. 19, then the system will automatically implement a different insulin delivery strategy such as limiting the insulin delivery only to minimal basal amounts, and both sensors would be signaled to be replaced. In addition, if the total error $E_t$ does not exceed the threshold, no error comparison will be made between the two sensors. Instead, only the predicted sensor values of the first sensor 800 will be used.

While the description above refers to particular embodiments of the present invention, it will be understood that many modifications may be made without departing from the spirit thereof. For example, additional steps and changes to the order of the algorithms can be made while still performing the key teachings of the present invention. In addition, although the preferred embodiments described the use of two sensors, in alternative embodiments three or more sensors can be used with the present invention. Thus, the accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method of sensing blood glucose values using redundant sensors, comprising:
    obtaining a first glucose reading from a first glucose sensor located at a first site;
    obtaining a second glucose reading from a second glucose sensor located at a second site;
    deriving a first predictive value for the first glucose sensor corresponding to the first glucose reading using the second glucose reading as an input;
    deriving a second predictive value for the second glucose sensor corresponding to the second glucose reading using the first glucose reading as an input;
    determining a first error between the first predictive value and the first glucose reading;
    determining a second error between the second predictive value and the second glucose reading;
    comparing a sum of the absolute error values of the first and second errors to a threshold;
    determining a failing sensor exists if the sum of the absolute error values exceed the threshold;
    determining whether the first glucose sensor or second glucose sensor has the least error in the sensor signal if the sum of the absolute error values does not exceed the threshold;
    calculating a blood glucose value based on the glucose sensor having the least error in the sensor signal; and
    reporting the calculated blood glucose value.

2. The method of claim 1, further comprising:
    requesting a meter glucose value if the sum of the absolute values exceed the threshold; and
    comparing the meter glucose value to the first and second glucose readings to determine if the first or second glucose sensor is failing.

3. The method of claim 1, wherein the first glucose sensor and the second glucose sensor use different types of technology.

4. The method of claim 1, wherein the first site is subcutaneous tissue, and the second site is blood plasma.

5. The method of claim 1, wherein the first site and the second site is subcutaneous tissue.

6. The method of claim 1, wherein the second sensor acts as a watchdog for the first sensor.

7. The method of claim 1, wherein the steps of deriving a first predictive value and deriving a second predictive value uses a first and a second adaptive filter.

8. The method of claim 1, wherein the reported blood glucose value is calculated based on the predictive value for the glucose sensor having the least error in the sensor signal.

9. The method of claim 1, wherein the reported blood glucose value is calculated based on the glucose reading for the glucose sensor having the least error in the sensor signal.

10. The method of claim 1, wherein the reported blood glucose value is calculated based on the glucose sensor having the least error in the sensor signal and a calibration factor for calibrating the sensor signal from the glucose sensor having the least error in the sensor signal.

11. A closed loop system or semi-closed loop system for infusing insulin using sensor values comprising:
    an infusion pump delivering insulin based on a reported blood glucose value derived by a controller configured to perform the steps of: obtaining a first glucose reading from a first glucose sensor located at a first site; obtaining a second glucose reading from a second glucose sensor located at a second site; deriving a first predictive value for the first glucose sensor corresponding to the first glucose reading using the second glucose reading as an input; deriving a second predictive value for the second glucose sensor corresponding to the second glucose reading using the first glucose reading as an input; determining a first error between the first predictive value and the first glucose reading; determining a second error between the second predictive value and the second glucose reading; comparing a sum of the absolute error values of the first and second errors to a threshold; determining a failing sensor exists if the sum of the absolute error values exceeds the threshold; determining whether the first glucose sensor or second glucose sensor has the least error in the sensor signal if the sum of the absolute error values does not exceed the threshold; calculating a blood glucose value based on the glucose sensor having the least error in the sensor signal; and reporting the calculated blood glucose value.

12. A system of sensing blood glucose values using redundant sensors, comprising:
    means for obtaining a first glucose reading from a first glucose sensor located at a first site;
    means for obtaining a second glucose reading from a second glucose sensor located at a second site;
    means for deriving a first predictive value for the first glucose sensor corresponding to the first glucose reading using the second glucose reading as an input;
    means for deriving a second predictive value for the second glucose sensor corresponding to the second glucose reading using the first glucose reading as an input;
    means for determining a first error between the first predictive value and the first glucose reading;
    means for determining a second error between the second predictive value and the second glucose reading;
    means for comparing a sum of the absolute error values of the first and second errors to a threshold;
    means for determining a failing sensor exists if the sum of the absolute error values exceed the threshold;
    means for determining whether the first glucose sensor or second glucose sensor has the least error in the sensor signal if the sum of the absolute error values does not exceed the threshold;
    means for calculating a blood glucose value based on the glucose sensor having the least error in the sensor signal; and
    means for reporting the calculated blood glucose value.

13. The system of claim 12, further comprising:
    means for requesting a meter glucose value if the sum of the absolute values exceed the threshold; and
    means for comparing the meter glucose value to the first and second glucose reading to determine if the first or second glucose sensor is failing.

14. The system of claim 12, wherein the first glucose sensor and the second glucose sensor use different types of technology.

15. The system of claim 12, wherein the first site is subcutaneous tissue, and the second site is blood plasma.

16. The system of claim 12, wherein the first site and the second site is subcutaneous tissue.

17. The system of claim 12, wherein the second sensor acts as a watchdog for the first sensor.

18. The system of claim 12, wherein the steps of deriving a first predictive value and deriving a second predictive value uses a first and a second adaptive filter.

19. The system of claim 12, wherein the reported blood glucose value is calculated based on the predictive value for the glucose sensor having the least error in the sensor signal.

20. The system of claim 12, wherein the reported blood glucose value is calculated based on the glucose reading for the glucose sensor having the least error in the sensor signal.

21. The system of claim 12, wherein the reported blood glucose value is calculated based on the glucose sensor having the least error in the sensor signal and a calibration factor for calibrating the sensor signal from the glucose sensor having the least error in the sensor signal.

* * * * *